US007258664B2

(12) United States Patent
Nishimura et al.

(10) Patent No.: US 7,258,664 B2
(45) Date of Patent: Aug. 21, 2007

(54) ENDOSCOPE INSERTING DIRECTION DETECTING METHOD AND ENDOSCOPE INSERTING DIRECTION DETECTING SYSTEM

(75) Inventors: Hirokazu Nishimura, Hachioji (JP); Tetsuo Nonami, Hino (JP)

(73) Assignee: Olympus Corporation, Tokyo (JP)

( * ) Notice: Subject to any disclaimer, the term of this patent is extended or adjusted under 35 U.S.C. 154(b) by 509 days.

(21) Appl. No.: 10/797,714

(22) Filed: Mar. 10, 2004

(65) Prior Publication Data

US 2005/0010082 A1 Jan. 13, 2005

Related U.S. Application Data

(63) Continuation of application No. PCT/JP02/09754, filed on Sep. 24, 2002.

(30) Foreign Application Priority Data

Sep. 25, 2001 (JP) ............................. 2001-292230

(51) Int. Cl.
*A61B 1/04* (2006.01)
(52) U.S. Cl. ...................... 600/117; 600/118; 600/103; 600/109
(58) Field of Classification Search ................ 600/103, 600/109, 117, 118
See application file for complete search history.

(56) References Cited

U.S. PATENT DOCUMENTS

| 4,910,590 | A | | 3/1990 | Gillies et al. |
| 4,916,533 | A | | 4/1990 | Gillies et al. |
| 5,018,509 | A | * | 5/1991 | Suzuki et al. ............... 600/115 |
| 5,036,464 | A | * | 7/1991 | Gillies et al. ............... 600/145 |
| 5,347,987 | A | * | 9/1994 | Feldstein et al. ........... 600/109 |
| 5,469,254 | A | * | 11/1995 | Konomura ............... 356/241.1 |
| 5,469,840 | A | | 11/1995 | Tanii et al. |
| 5,658,238 | A | * | 8/1997 | Suzuki et al. ............... 600/150 |
| 5,951,461 | A | * | 9/1999 | Nyo et al. .................. 600/118 |
| 2006/0015011 | A1 | * | 1/2006 | Hasegawa et al. .......... 600/117 |

FOREIGN PATENT DOCUMENTS

| GB | 2 225 188 A | 5/1990 |
| GB | 2 227 836 A | 8/1990 |
| JP | 2-140134 | 5/1990 |
| JP | 2-182231 | 7/1990 |
| JP | 3-85134 | 4/1991 |
| JP | 5-211990 | 8/1993 |
| JP | 7-136109 | 5/1995 |
| JP | 2001-169998 | 6/2001 |

\* cited by examiner

*Primary Examiner*—John P Leubecker
(74) *Attorney, Agent, or Firm*—Scully, Scott, Murphy & Presser, P.C.

(57) ABSTRACT

An endoscope inserting direction detecting system receives an endoscopic image, detects an endoscope inserting direction, in which an endoscope should be inserted, on the basis of the endoscopic image and produces information concerning the detected inserting direction. A plurality of detecting algorithms, each of which detect the inserting direction, are included and any of the plurality of detecting algorithms can be selected based on the endoscopic image.

3 Claims, 20 Drawing Sheets

DIRECTION OF LUMEN

HALATION

HALATION
FINING

• SAMPLING-PIXEL

SEARCHED RANGE
FOR ARC CENTER

FIG.23
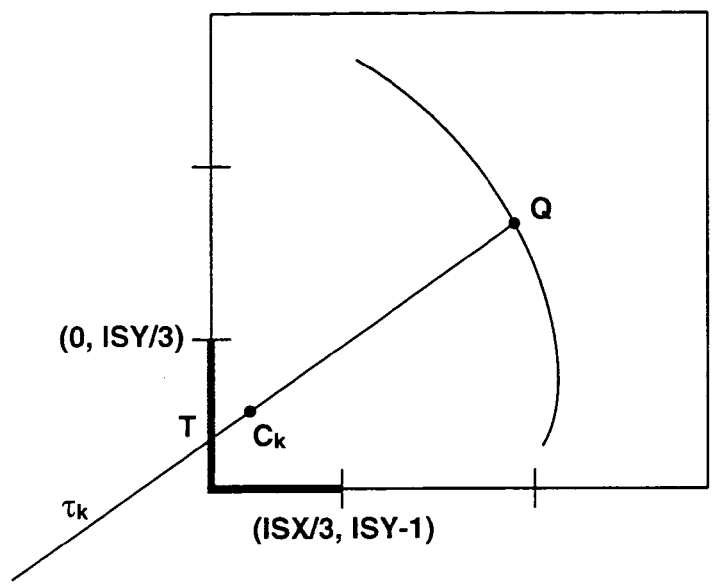
FIG.24A        FIG.24B
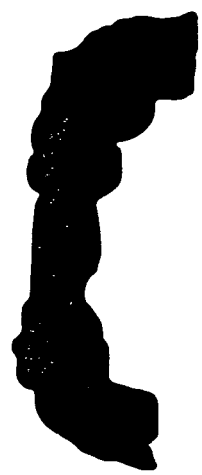 ⇒ 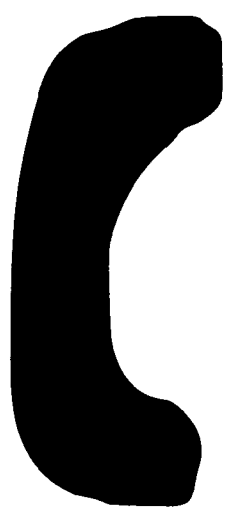
BINARY-CODED
IMAGE
EXPANDED
BINARY-CODED
IMAGE

FIG.25A FIG.25B
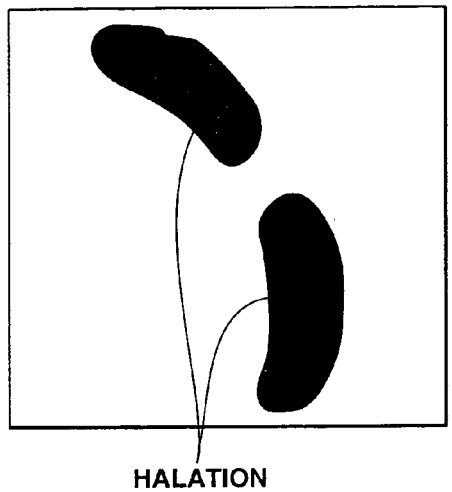
HALATION
→ FINING →
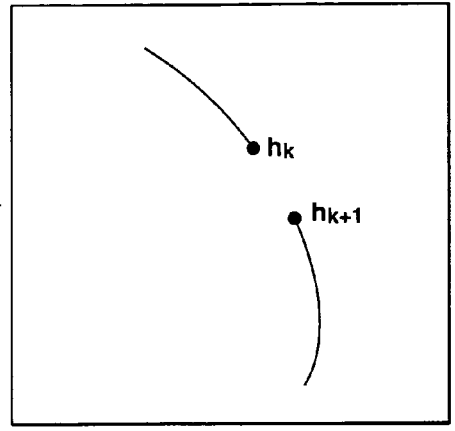
FIG.26
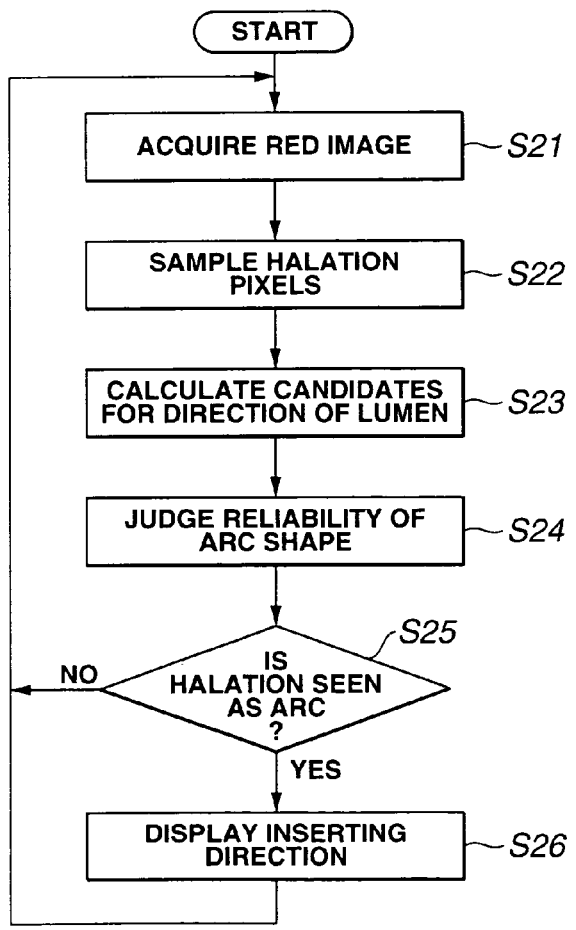

RAW IMAGE (RED IMAGE)

BINARY-CODED IMAGE OF SHADE

ENDOSCOPE INSERTING DIRECTION DETECTING METHOD AND ENDOSCOPE INSERTING DIRECTION DETECTING SYSTEM

This application is a continuation of prior application No. PCT/JP02/09754, filed Sep. 24, 2002.

TECHNICAL FIELD

The present invention relates to an endoscope inserting direction detecting method and an endoscope inserting direction detecting system. More particularly, the present invention is concerned with an endoscope inserting direction detecting method and an endoscope inserting direction detecting system which assist in observing or examining an object having a luminal structure, such as, the large intestine in the field of medicine or pipes in the field of industries.

BACKGROUND ART

In recent years, medical-purpose endoscopes have been widely adopted in order to observe an intracavitary organ by inserting an elongated insertion unit, which has flexibility, into a body cavity, or to perform various cures or treatments with a treatment instrument passed through a channel that lies through the insertion unit. Moreover, industrial-purpose endoscopes have been used to observe internal corrosive states of pipes in buildings.

For insertion of an endoscope in various examinations, a doctor or an engineer who is an operator judges a direction of advancement while viewing an endoscopic image.

On the other hand, an inserting procedure for examining the large intestine is hard to do and requires expertise. This is because the shape of the large intestine is complex, the lumen of the large intestine is narrow, and the shape of the large intestine or the lumen thereof is different from person to person. Moreover, since insertion must be performed reliably and carefully, a doctor who has little experience incurs a large load.

An endoscope is inserted basically in a direction in which a lumen extends. However, the direction of a lumen is not always seen within a field of view offered by an endoscope system. When the endoscope has approached a tortuous region of the large intestine (the sigmoid colon, a curvature of the liver or spleen, or the like) or an intestinal wall or fold thereof, a doctor who is an operator must judge from his/her experience and knowledge in what direction the endoscope should be inserted.

In order to cope with the above situation, a doctor has to experience many examinations so as to be able to determine under various criteria in what direction the endoscope should be inserted.

However, a doctor who is inexperienced has a little knowledge or experience in determining what information should be used to make a judgement in what manner. Consequently, it becomes necessary to withdraw an endoscope for the purpose of catching a lumen in a field of view again. This leads to an increase in examination time or patient discomfort.

Moreover, when an endoscope is used to examine pipes in the field of industries, an operator who inserts the endoscope into a pipe has to incur a large load because of the complex bending of pipes.

On the other hand, Japanese Patents Nos. 2710384 and 2680111 have disclosed inserting direction detecting techniques. However, these techniques aim to detect a lumen seen within a field of view for imaging but do not have the advantage of detecting an inserting direction in case the lumen disappears from the field of view.

The present invention attempts to break through the foregoing situation. An object of the present invention is to provide an endoscope inserting direction detecting method for detecting an inserting direction in case a lumen disappears from a field of view for imaging.

Another object of the present invention is to provide an endoscope inserting direction detecting system capable of assisting in performing endoscopic examination smoothly by providing an operator with information of an inserting direction on the basis of the result of inserting direction detection.

Still another object of the present invention is to provide an endoscope inserting direction detecting method capable of prompting an operator to perform an appropriate manipulation in case an endoscope approaches too closely the mucosal surface of the lumen of the large intestine or in case there is difficulty in detecting an inserting direction.

DISCLOSURE OF INVENTION

An endoscope inserting direction detecting method in accordance with the present invention consists mainly of: a first step of receiving an endoscopic image; a second step of detecting the direction of a change in brightness in the endoscopic image; and a third step of producing information concerning an endoscope inserting direction, in which an endoscope should be inserted, on the basis of the result of the detection.

Another endoscope inserting direction detecting method in accordance with the present invention consists mainly of: a first step of determining inserting-direction candidates, that is, candidates for an endoscope inserting direction in which an endoscope should be inserted; a second step of receiving an endoscopic image; a third step of detecting the direction of a change in brightness in the endoscopic image; a fourth step of evaluating the similarities among a plurality of the inserting-direction candidates and the direction of the change in brightness; and a fifth step of determining an endoscope inserting direction on the basis of the evaluation.

Still another endoscope inserting direction detecting method in accordance with the present invention consists mainly of: a first step of receiving an endoscopic image; a second step of sampling pixels, which represent high densities, from data of the endoscopic image; a third step of defining an approximate expression for providing an approximate state of a distribution of sampling-pixels; and a fourth step of determining an endoscope inserting direction, in which an endoscope should be inserted, on the basis of the result of the approximation.

Still another endoscope inserting direction detecting method in accordance with the present invention consists mainly of: a first step of receiving an endoscopic image; a second step of sampling pixels, which represent high densities, from data of the endoscopic image; a third step of determining a direction based on a combination of sampling-pixels; and a fourth step of determining an endoscope inserting direction, in which an endoscope should be inserted, on the basis of the determined direction.

Still another endoscope inserting direction detecting method in accordance with the present invention consists mainly of: a first step of receiving an endoscopic image; a second step of sampling pixels, which represent high densities, from data of the endoscopic image; a third step of defining an approximate expression for providing an approximate state of a distribution of sampling-pixels; a fourth step of evaluating a difference between the distribution of sampling-pixels and the result of the approximation; a fifth step of determining an endoscope inserting direction, in which an endoscope should be inserted, on the basis of the distribution of sampling-pixels; and a sixth step of producing information concerning the determined inserting direction. Herein, if the result of the approximation proves unsatisfactory at the step of evaluating a difference from the result of the approximation, at least either of determination of an inserting direction or production of information is not performed.

Still another endoscope inserting direction detecting method in accordance with the present invention consists mainly of: a first step of receiving endoscopic images time-sequentially; a second step of detecting the direction of a shift in the plurality of time-sequentially-received endoscopic images; and a third step of determining an endoscope inserting direction, in which an endoscope should be inserted, on the basis of the result of the detection performed at the first step.

Still another endoscope inserting direction detecting method in accordance with the present invention consists mainly of: a first step of receiving an endoscopic image; a second step of detecting an endoscope inserting direction, in which an endoscope should be inserted, on the basis of the endoscopic image; and a third step of producing information concerning the detected inserting direction. Herein, a plurality of detecting algorithms according to which an inserting direction is detected is included, and any of the detecting algorithms is selected based on the endoscopic image.

An endoscope inserting direction detecting system in accordance with the present invention consists mainly of: an endoscopic image inputting means for receiving an endoscopic image; an inserting direction detecting means including a plurality of detecting algorithms according to which an endoscope inserting direction in which an endoscope should be inserted is detected depending on the endoscopic image; an insertion aid information producing means for producing insertion aid information on the basis of the detected inserting direction. Herein, the inserting direction detecting means includes a detecting algorithm changing means for changing the detecting algorithms, any of which the inserting direction detecting means adopts, according to the endoscopic image.

Another endoscope inserting direction detecting method in accordance with the present invention consists mainly of: a first step of receiving an endoscopic image; a second step of judging from the endoscopic image whether an endoscope has approached too closely an object of observation; and a third step of producing information concerning manipulations of the endoscope on the basis of the result of the detection.

BRIEF DESCRIPTION OF THE DRAWINGS

FIG. 23 is an explanatory diagram concerning a method of determining the direction of a lumen during the processing described in FIG. 18;

FIG. 24A is an explanatory diagram before expansion that is performed during the processing in FIG. 18;

FIG. 24B is an explanatory diagram after expansion has been performed during the processing in FIG. 18;

FIG. 25A is an explanatory diagram concerning the contents of the processing in FIG. 18 performed when a plurality of halations exist before fining is performed;

FIG. 25B is an explanatory diagram concerning the contents of the processing in FIG. 18 performed when a plurality of halations exist after fining has been performed;

FIG. 26 is a flowchart describing inserting direction detection in accordance with a third embodiment of the present invention;

BEST MODE FOR CARRYING OUT THE INVENTION

Figure 1:
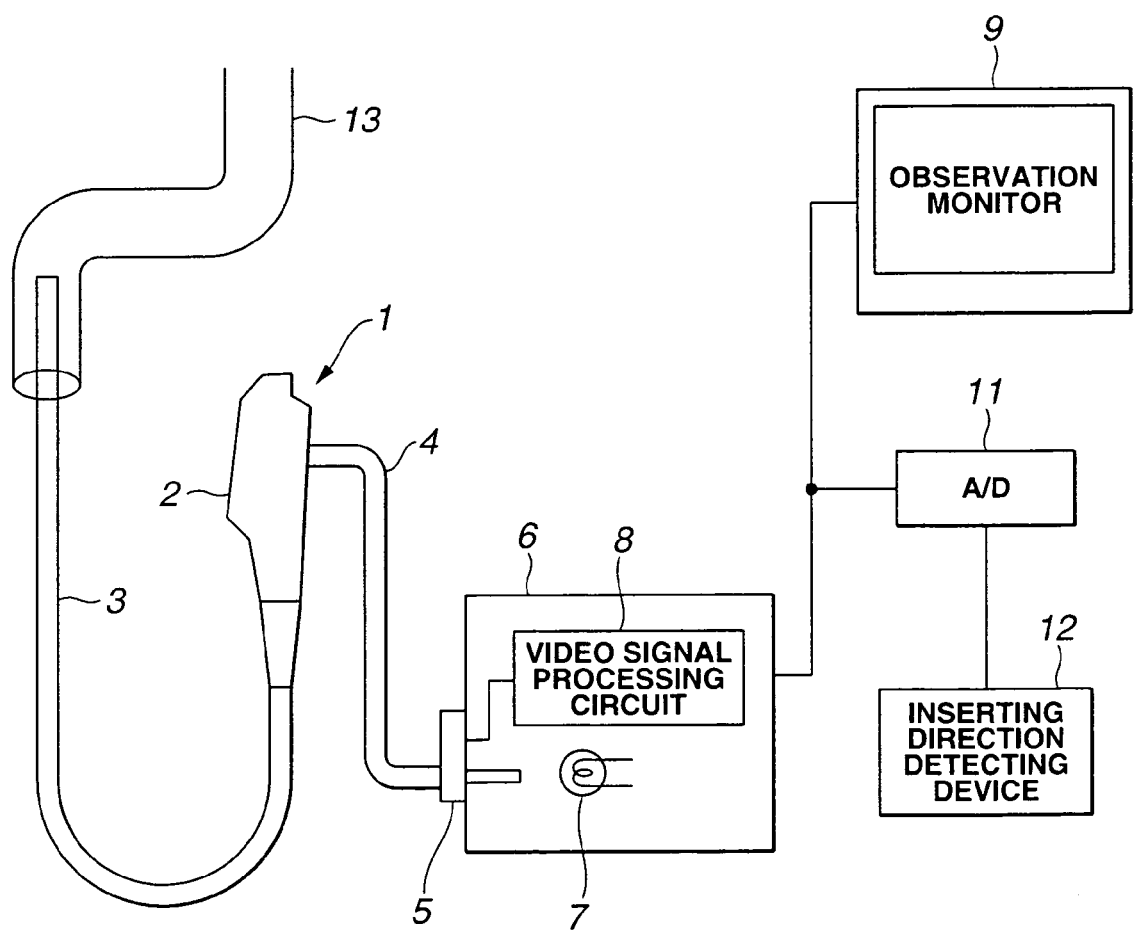
FIG. 1 shows an overall configuration of an endoscope system in which a first embodiment of the present invention is included.

Referring to the drawings, embodiments of the present invention will be described below.

Hereinafter, a description will be made of detection of an inserting direction that is performed in order to insert an endoscope into the large intestine. The same can apply to insertion of an endoscope into pipes or a tubular object that is performed in the field of industries. In general, pipes are more rigid than the large intestine that is an intracavitary organ. Moreover, an object does not make a motion stemming from pulsation or the like. Therefore, conditions for detection of an inserting direction are loose. Consequently, the present invention will prove quite advantageous in the field of industries.

Moreover, the embodiments of the present invention aim mainly to present endoscope insertion aid information, which is acquired during inserting direction detection, to an operator. The present invention can also apply to automatic insertion that is combined with automatic manipulations of an endoscope. In this case, automatic endoscope manipulations are controlled so that the endoscope will advance in a detected inserting direction.

First Embodiment

Figure 2:
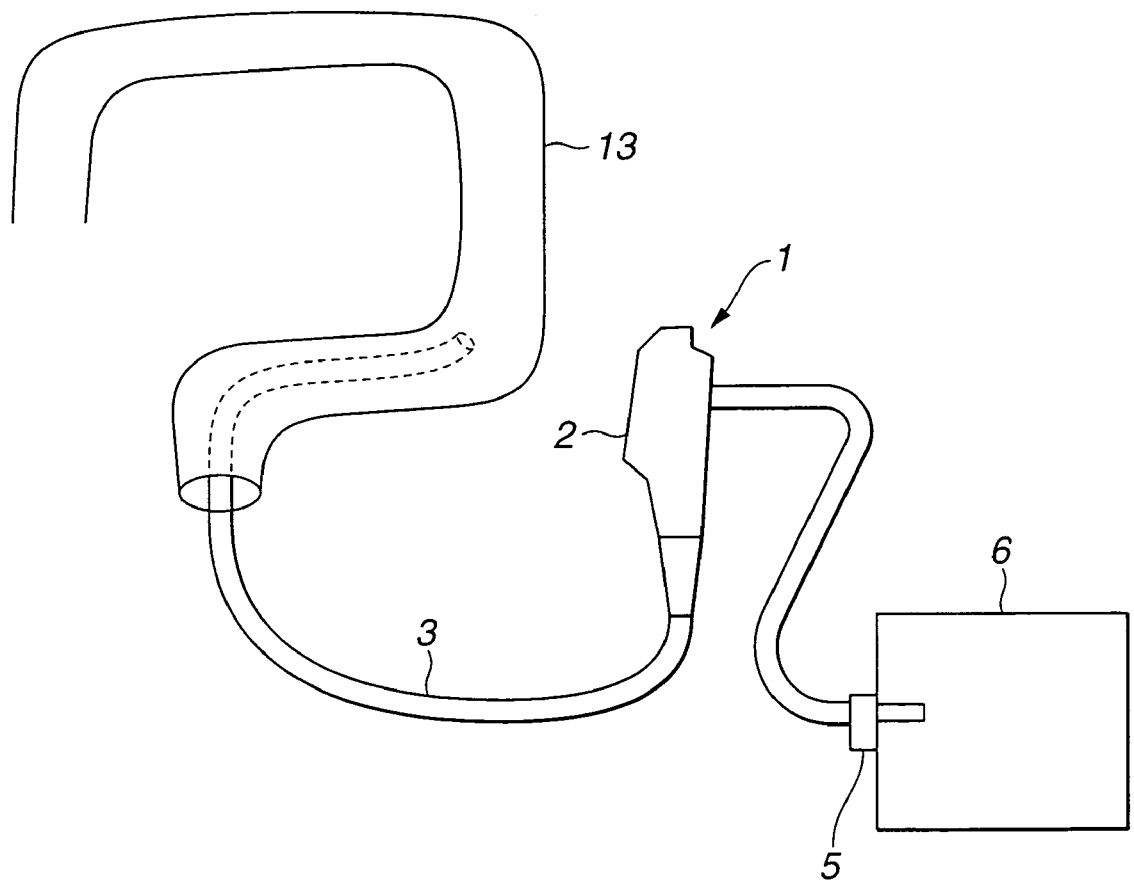
FIG. 2 is an explanatory diagram for explaining insertion of an endoscope shown in FIG. 1.
Figure 3:
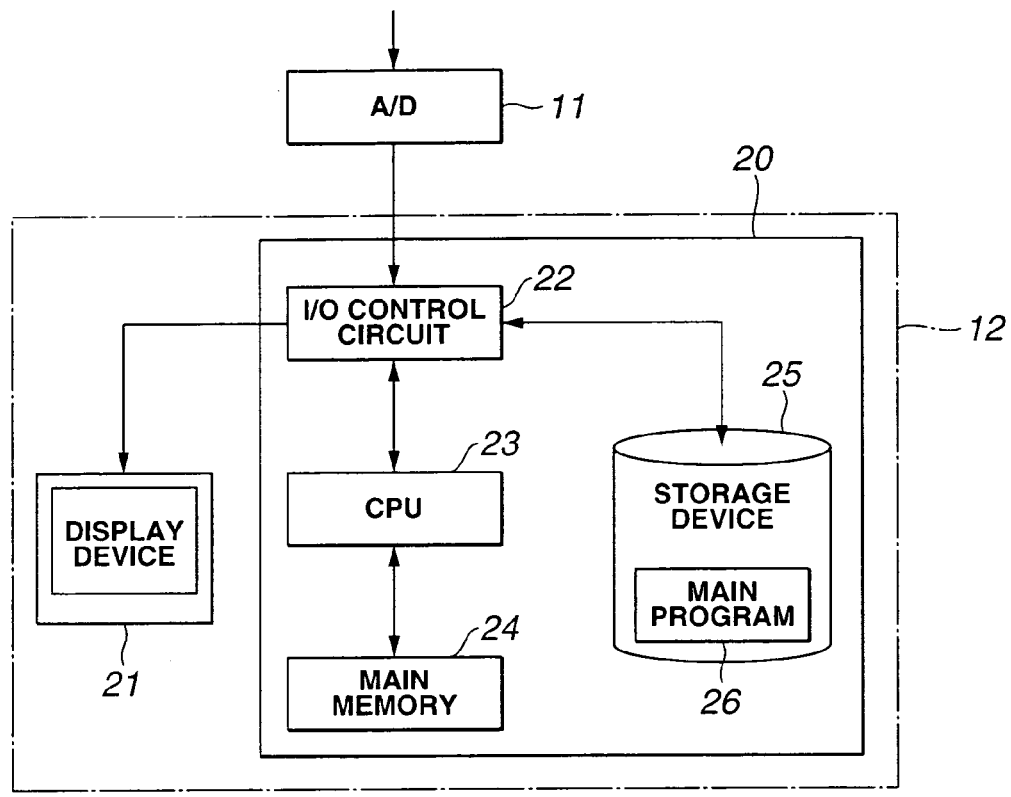
FIG. 3 shows the configuration of an inserting direction detecting system shown in FIG. 1.
Figure 4:
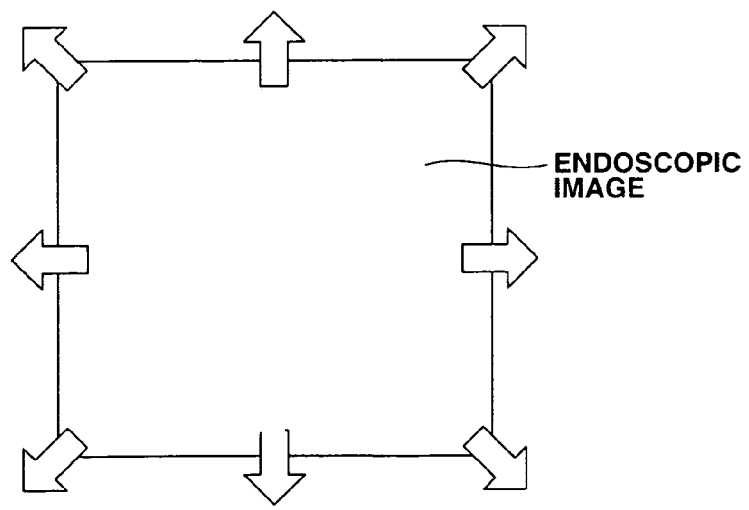
FIG. 4 is an explanatory diagram concerning display of inserting directions by a display device included in the inserting direction detecting system shown in FIG. 3.
Figure 5:
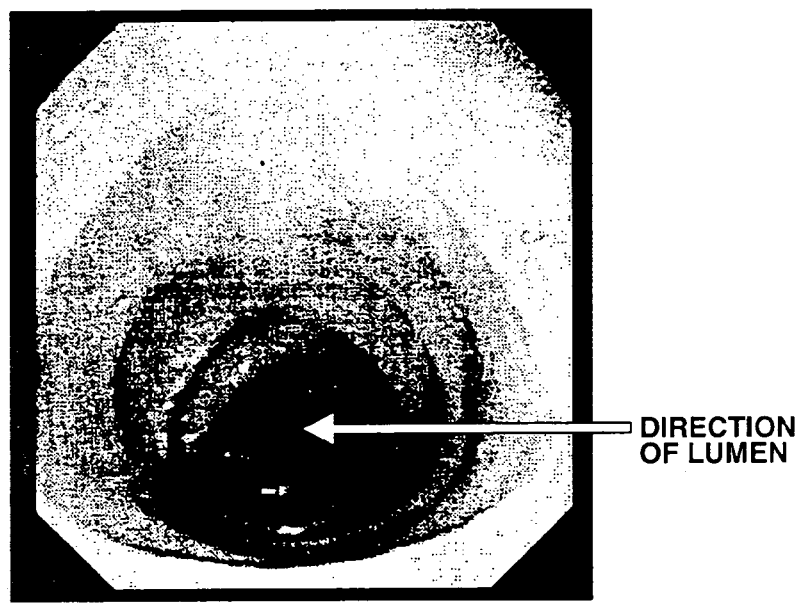
FIG. 5 is a first explanatory diagram showing an example of an endoscopic image to be used to judge an inserting direction by the inserting direction detecting system shown in FIG. 3.
Figure 6:
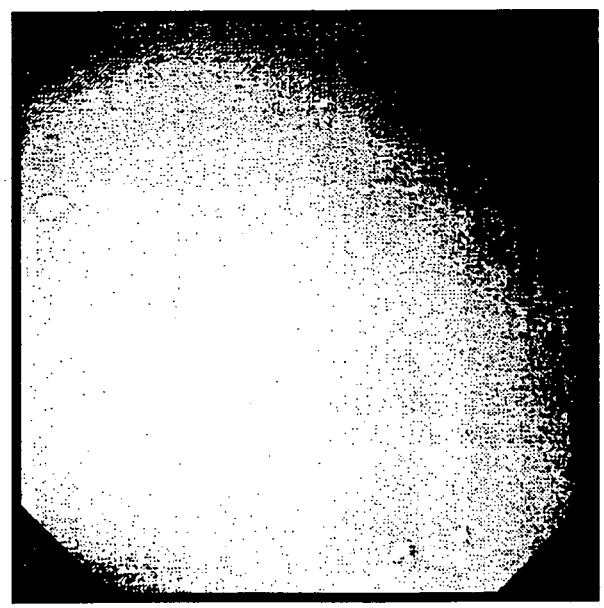
FIG. 6 is a second explanatory diagram showing an example of an endoscopic image to be used to judge an inserting direction by the inserting direction detecting system shown in FIG. 3.
Figure 7:
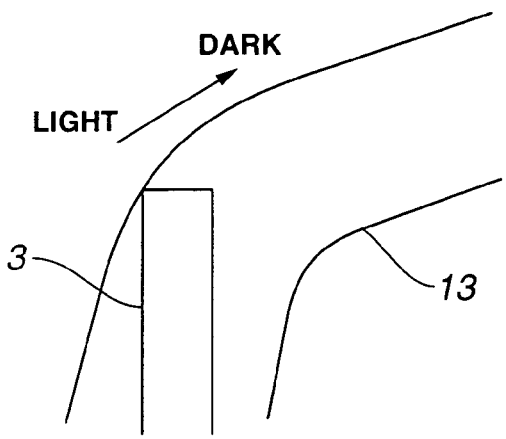
FIG. 7 is an explanatory diagram showing an inserted state of the endoscope shown in FIG. 1.
Figure 8:
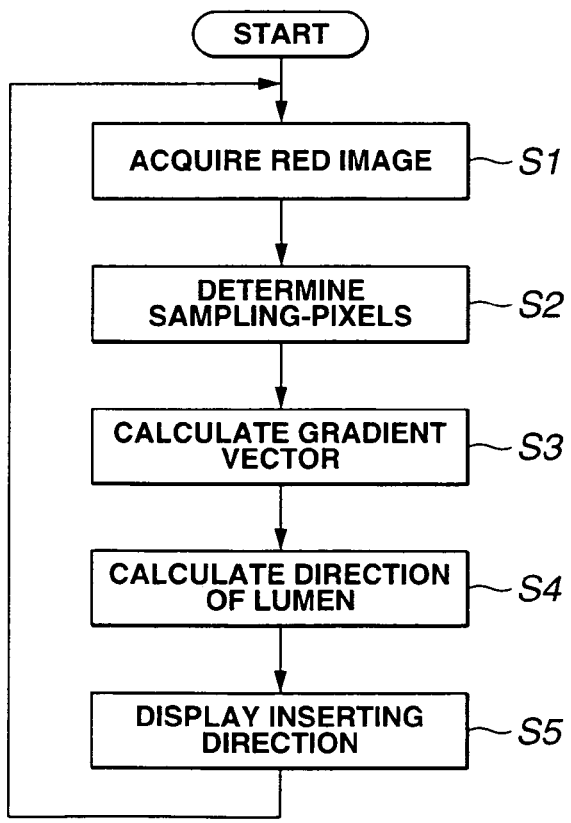
FIG. 8 is a flowchart describing inserting direction detection to be performed by the inserting direction detecting system shown in FIG. 3.
Figures 9, 10:
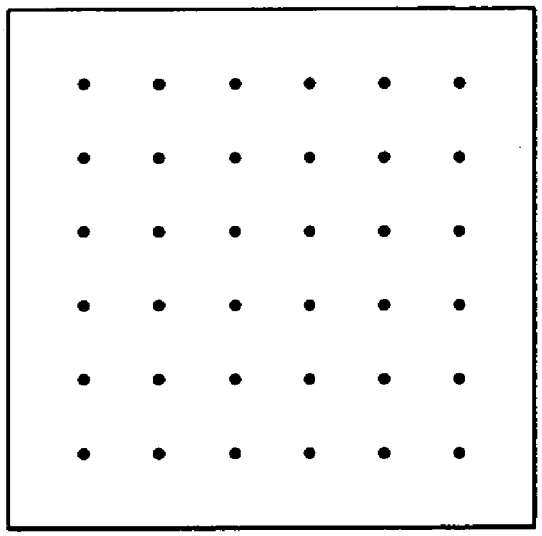
FIG. 9 is an explanatory diagram for explaining sampling-pixels to be determined in order to detect the direction of a lumen during the processing described in FIG. 8.
FIG. 10 is an explanatory diagram for explaining a spatial differentiation geometric procedure to be performed in order to calculate a gradient vector during the processing described in FIG. 8.
Figure 11:
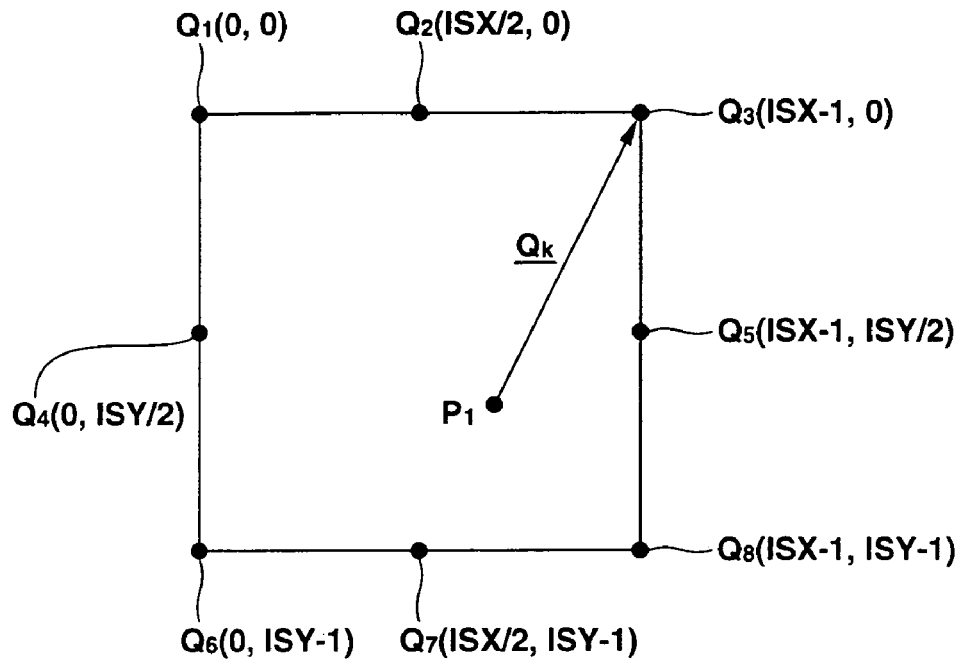
FIG. 11 is a first explanatory diagram for explaining direction-of-lumen detection that is performed based on a gradient vector during the processing described in FIG. 8.
Figure 12:
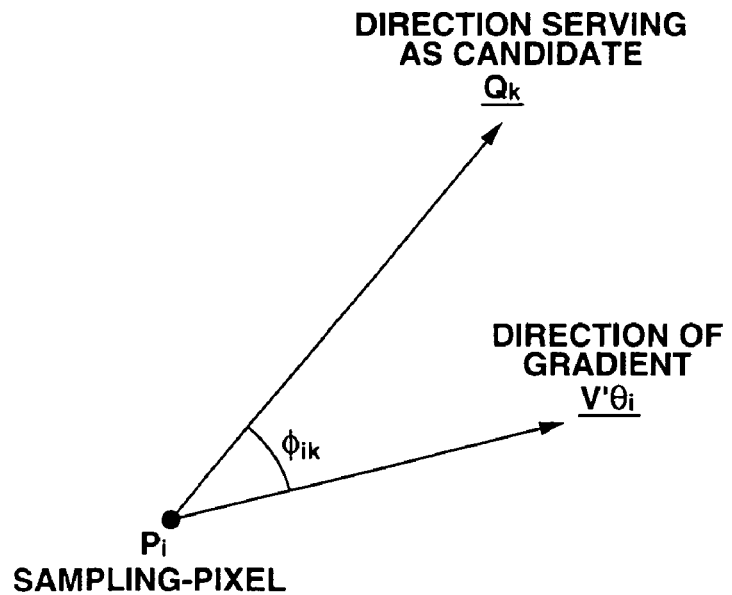
FIG. 12 is a second explanatory diagram for explaining direction-of-lumen detection that is performed based on a gradient vector during the processing described in FIG. 8.
Figure 13:
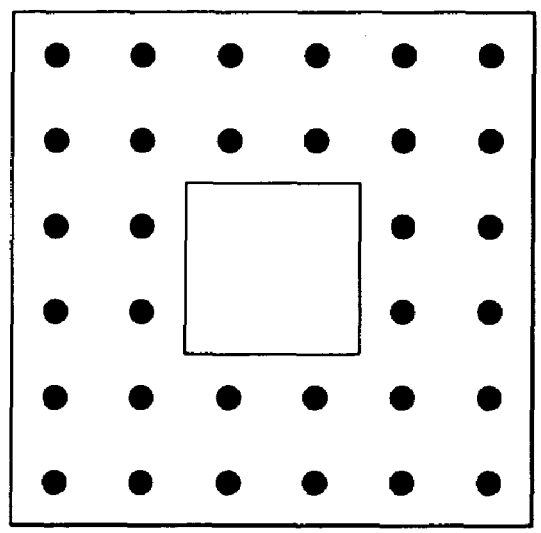
FIG. 13 is an explanatory diagram concerning other sampling-pixels to be determined during the processing described in FIG. 8.
Figure 14:
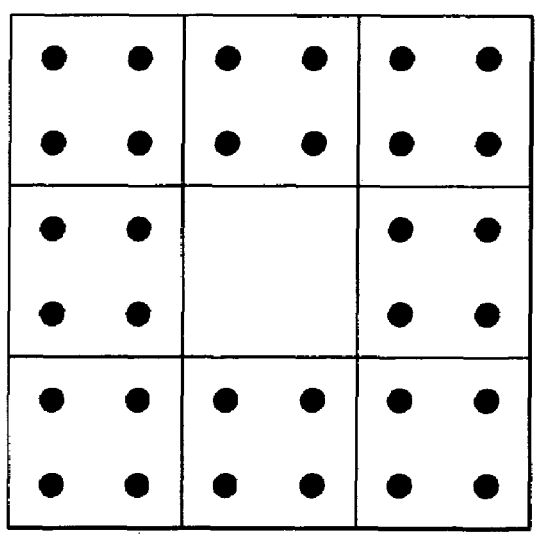
FIG. 14 is an explanatory diagram concerning domain division to be performed during the processing described in FIG. 8.
Figure 15:
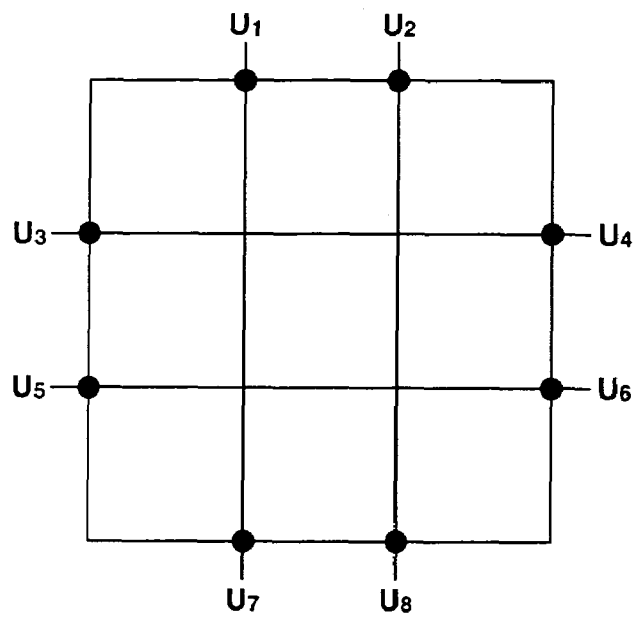
FIG. 15 is an explanatory diagram for explaining division that is performed in order to associate the outline of an image with the direction of a lumen during the processing described in FIG. 8.
Figure 16:
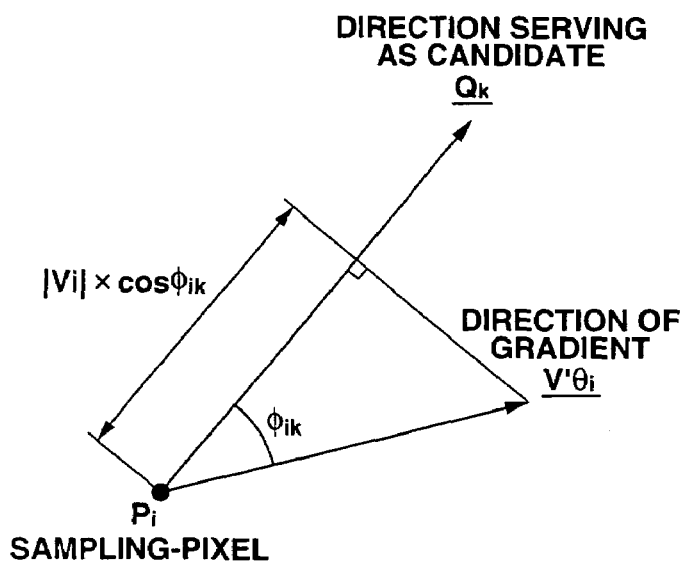
FIG. 16 is an explanatory diagram concerning projection of a vector to be performed during the processing described in FIG. 8.

FIG. 1 to FIG. 16 are concerned with a first embodiment of the present invention. FIG. 1 shows the overall configuration of an endoscope system. FIG. 2 is an explanatory diagram concerning insertion of an endoscope shown in FIG. 1. FIG. 3 shows the configuration of an inserting direction detecting system shown in FIG. 1. FIG. 4 is an explanatory diagram concerning display of an inserting direction on a display device included in the inserting direction detecting system shown in FIG. 3. FIG. 5 is a first explanatory diagram showing an example of an endoscopic image based on which an inserting direction is judged by the inserting direction detecting system shown in FIG. 3. FIG. 6 is a second explanatory diagram showing an example of an endoscopic image based on which an inserting direction is judged by the inserting direction detecting system shown in FIG. 3. FIG. 7 is an explanatory diagram concerning an inserted state of the endoscope shown in FIG. 1. FIG. 8 is a flowchart describing inserting direction detection to be performed by the inserting direction detecting system shown in FIG. 3. FIG. 9 is an explanatory diagram concerning sampling-pixels to be determined for direction-of-lumen detection during the processing described in FIG. 8. FIG. 10 is an explanatory diagram concerning a spatial differentiation geometric procedure for calculating a gradient vector during the processing described in FIG. 8. FIG. 11 is a first explanatory diagram concerning direction-of-lumen detection to be performed based on a gradient vector during the processing described in FIG. 8. FIG. 12 is a second explanatory diagram concerning direction-of-lumen detection to be performed based on a gradient vector during the processing described in FIG. 8. FIG. 13 is an explanatory diagram concerning other sampling-pixels to be determined during the processing described in FIG. 8. FIG. 14 is an explanatory diagram concerning domain division to be performed during the processing described in FIG. 8. FIG. 15 is an explanatory diagram concerning division to be performed in order to associate the outline of an image with the direction of a lumen during the processing described in FIG. 8. FIG. 16 is an explanatory diagram concerning projection of a vector to be performed during the processing described in FIG. 8.

Described as the first embodiment of the present invention is an inserting direction detecting method for determining the direction of a lumen according to the direction of a gradient in brightness in case the lumen disappears from a field of view for imaging. Also described is an inserting direction detecting system that presents inserting direction information to an operator on the basis of the result of processing performed according to the method so as to assist in performing endoscopic examination more smoothly.

To begin with, referring to FIG. 1, an endoscope system in which the present embodiment is included will be described below. Referring to FIG. 1, the endoscope system in which the present embodiment is included consists mainly of an endoscope 1, a controller 6, an observation monitor 9, an inserting direction detecting system 12 that detects and displays an inserting direction, and an A/D converter 11.

The endoscope 1 has an operating unit 2 and an insertion unit 3 that is flexible. A solid-state imaging device (CCD) and a light guide end from which illumination light is emitted are incorporated in the distal part of the insertion unit 3. Moreover, the endoscope 1 is connected to a video signal processing circuit 8 via a connector 5.

The endoscope 1 has an optical fiber over which illumination light is propagated and a universal cord 4 over which a video signal and various kinds of control information are transmitted or received. The insertion unit 3 is inserted into the large intestine 13, whereby image information of an intracavitary region is acquired.

The controller 6 includes a light source 7 that generates illumination light which is propagated to the endoscope 1, and a video signal processing circuit 8 that performs signal processing on a video signal sent from the endoscope 1.

By the controller 6, image information of a visualized intracavitary region is transferred as analog red, green, and blue signals to the observation monitor 9, digitized by the A/D converter 11, and transferred to the inserting direction detecting system 12.

Next, referring to FIG. 2, a description will be made of insertion of the endoscope by taking examination of the large intestine for instance. When the endoscope 1 is used to examine the large intestine, as shown in FIG. 2, the insertion unit 3 of the endoscope 1 that is elongated and flexible is inserted into the large intestine 13. Thus, an intracavitary region is observed. For insertion, a doctor who is an operator holds an angle knob which is not shown and is included in the operating unit 2 (an operating member for use in angling the distal part of the endoscope upwards, downwards, rightwards, or leftwards by way of wires or the like lying through the insertion unit 3). The doctor then exploits a technique for angling the distal part of the endoscope or techniques of thrusting, withdrawing, and twisting the insertion unit 3. Thus, the doctor observes a region extending from the anus to the ileocecum that is the deepest region (linking the small intestine and the large intestine).

Next, referring to FIG. 3, the configuration of the inserting direction detecting system 12 in accordance with the present embodiment will be described below.

As shown in FIG. 3, the inserting direction detecting system 12 includes: a computer 20 that follows a series of steps so as to perform inserting direction detection on red, green, and blue image signals received from the A/D converter 11; and a display device 21 on which the result of the inserting direction detection is displayed.

Furthermore, the computer 20 includes: a storage device 25 in which a main program 26 for detecting an inserting direction is stored; a central processing unit (CPU) 23 for executing inserting direction detection to be performed according to the main program 26; a main memory 24; and an I/O control circuit 22 for controlling the inputs and outputs of the A/D converter 11, storage device 25, display device 21, and CPU 23.

The main program 26 is a program describing a series of steps required for inserting direction detection of the present embodiment. Within the main program 26, a request for acquisition of an image signal from the A/D converter 11 is issued to the I/O control circuit 22, and a request for display of the result of inserting direction detection is issued to the display device 21.

According to the present embodiment, an endoscopic image is digitized by the A/D converter 11 so that each of red, green, and blue signals will be quantized into a series of levels which range from level 0 to level 255 and each of which is represented by eight bits. The resultant image data shall have a size of ISX in a horizontal direction and a size of ISY in a vertical direction. Hereinafter, a description will proceed on the assumption that a left upper limit that is a location of one of pixels constituting endoscopic image data shall be represented by coordinates (0,0) and a right lower limit shall be represented by coordinates (ISX-1, ISY-1).

Next, a description will be made of an example of display of the result of inserting direction detection on the display device 21 included in the inserting direction detecting system 12.

The endoscope is inserted into a luminal organ such as the large intestine in a direction in which the lumen of the large intestine extends. In this case, the endoscope must be inserted accurately and safely with the lumen of the large intestine caught in a field of view for imaging. However, the lumen may disappear from the field of view for various reasons that will be described later. Moreover, a case where a doctor who has a little experience cannot decide in what direction the lumen extends takes place frequency. In this case, the endoscope 1 must be withdrawn (or pulled back) so that the lumen will enter the field of view. This results in an increase in examination time.

In the inserting direction detecting system 12 of the present embodiment, when a lumen is not visualized clearly as part of an endoscopic image, an inserting direction is detected by adopting an image processing technique. The information of the inserting direction is then presented to a doctor who performs examination. Thus, the present embodiment assists in achieving endoscopic examination smoothly.

Concrete inserting direction information is, as shown in FIG. 4, any of arrows indicating eight directions which is superposed on an endoscopic image. The eight directions are different from one another by 45°. A doctor who performs endoscopic examination angles the endoscope, thrusts or pulls it, or twists it so that the endoscope will advance in the direction of the superposed arrow. Thus, the doctor can catch the lumen in the field of view.

According to the present embodiment, for convenience sake, an inserting direction is determined as one of the eight directions. Alternately, the inserting direction may be selected from sixteen directions, which are different from one another by 22.5°, or more. The number of options can be determined appropriately according to the skill of a doctor who performs examination or the necessity.

Next, a description will be made of an inserting direction detecting method in accordance with the present embodiment.

A maneuver of inserting an endoscope for the purpose of examination of the large intestine ranks high in difficulty and requires a skill. This is because the shape of the large intestine is complex, the lumen thereof is narrow, and the shape and lumen of the large intestine differ from person to person. Since insertion must be performed accurately and carefully, the insertion imposes a heavy load on a doctor who has a little experience. Basically, an endoscope is inserted in a direction in which a lumen extends. However, the direction of the lumen is not always seen within a field of view offered by an endoscope system. When an endoscope approaches too closely a curved region of the large intestine (the sigmoid colon, or a curvature of the liver or spleen) or an intestinal wall or fold, a doctor who is an operator must judge an inserting direction from his/her experience or knowledge. In order to cope with such a situation, a doctor has to experience many examinations so as to be able to determine an inserting direction under various criteria.

Specifically, for example, in an endoscopic image shown in FIG. 5, a lumen is clearly seen within a field of view. It is therefore judged that an endoscope should be kept inserted rectilinearly. On the other hand, in an endoscopic image shown in FIG. 6, a lumen is not seen within the field of view.

An inserting direction, or in other words, a direction in which the lumen is found must therefore be judged from some information.

According to the present embodiment, as a technique for determining an inserting direction in case a lumen is not seen within a field of view, a direction detecting method that employs the direction of a gradient in brightness will be described below.

One of the criteria under which an inserting direction is judged in case a lumen is not seen within a field of view is the direction of a change in brightness in an image. For example, when the large intestine 13 and the distal part of the insertion unit 3 of the endoscope have a positional relationship shown in FIG. 7, a change in brightness occurs widely from a position near the distal end of the endoscope to a position far from it. There is a high possibility that an inserting direction is a direction receding from the distal end of the endoscope. Therefore, an inserting direction can be determined by detecting the direction of a change from a light to a shade in an image.

FIG. 8 describes a series of steps to be followed in order to perform inserting direction detection in accordance with the present embodiment. Herein, the processing is performed on data of each frame represented by an endoscopic image signal received via the A/D converter 11.

At step S1 in FIG. 8, a red image is acquired from among red, green, and blue images constituting a received endoscopic image. The processing in accordance with the present embodiment will be described by taking the red image for instance. The green or blue image or a luminance image (=0.3R+0.6G+0.1B) may be used to perform the same processing as the one described below.

At step S2, M sampling-pixels (where M denotes an integer equal to or larger than 1) are determined from data of the red image. The sampling-pixels are determined so that the whole image data can be sampled. FIG. 9 shows an example of sampling-pixels.

At step S3, a gradient vector is calculated in order to obtain the direction of a gradient in brightness in each sampling-pixel. In the present embodiment, a spatial differentiation geometric procedure is adopted as a technique for calculating a gradient vector. FIG. 10 is an explanatory diagram concerning a gradient vector calculating method based on the spatial differentiation geometric procedure.

First, as shown in FIG. 10, neighbor pixels arranged in N rows and N columns (N denotes 5 in FIG. 10) with a sampling-pixel P as a center are sampled. Pixels located at limits in horizontal and vertical directions and diagonal directions shall be regarded as pixels A, B, C, D, E, F, G, and H. Based on the pixel values, spatial differentiations SX and SY of pixel values arranged in the horizontal and vertical directions respectively are calculated as follows:

$$SX=(C+E+H)-(A+D+F) \quad (1)$$

$$SY=(F+G+H)-(A+B+C) \quad (2)$$

In the expressions (1) and (2), A, B, C, D, E, F, G, and H denote densities represented by the pixels.

Using the calculated SX and SY values, a gradient vector V (_ means a vector) is expressed as follows:

$$V=(SX, SY) \quad (3)$$

Moreover, the magnitude |V| of the gradient vector V, and the direction of a gradient V$\theta$ are calculated as follows:

$$\underline{V} = \sqrt{S_X^2 + S_Y^2} \quad (4)$$

$$V\theta = \tan^{-1}(SY/SX) \quad (5)$$

The foregoing gradient vector V is calculated for each of the M sampling-pixels. Herein, Vi (where i denotes 1, 2, etc., and/or M) denotes the gradient vector or vectors for each or all of the M sampling-pixels.

At step S4, direction-of-lumen detection is performed. The contents of direction-of-lumen detection employed in the present embodiment will be described in conjunction with FIG. 11 and FIG. 12.

Points on the outline of an image located in the eight directions described using FIG. 4 shall be points Qk (where k denotes, 1, 2, etc., or 8). Assuming that the image has a size of ISX by a size of ISY, coordinates representing the points are determined as shown in FIG. 11. The coordinates representing the points Qk shall be (qx, qy), and coordinates representing sampling-pixels Pi shall be (px, py). In this case, a vector $\underline{Qk}$ linking each point Qk and each pixel Pi are expressed as follows:

$$\underline{Qk}=(qx-px, qy-py) \quad (6)$$

A lumen is found in a direction of a change from a light to a shade in an image. Herein, V'$\theta$i shall denote an inverse vector of a gradient vector Vi representing a gradient in brightness in a sampling-pixel Pi (since the direction of a gradient expressed by the expression (5) is a direction of a change from a shade to a light, the gradient vector is inverted). The direction of a vector $\underline{Qk}$ from the pixel Pi to a point Qk that is located most closely to the inverse vector V'$\theta$i is regarded as the direction of the lumen.

Specifically, an angle $\phi$ik at which a vector $\underline{Qk}$ and an inverse vector V'$\theta$i meets as shown in FIG. 12 is calculated by solving expression (7) below.

$$\phi ik=\cos^{-1}\{(\underline{Qk}\cdot V'\theta i)/(|\underline{Qk}|\times|V'\theta i|)\} \quad (7)$$

where · denotes an inner product of two vectors, and | | denotes the magnitude of a vector.

The $\phi$ik value is larger than −180 and smaller than or equal to +180. Assuming that a lumen is found in a direction to a point Qk, that is, the direction of a gradient is close to the direction of a vector $\underline{Qk}$, the $\phi$ik value approaches 0 (units: degree).

Consequently, when the angle $\phi$ik is calculated relative to all sampling-pixels that lie in the direction of a lumen, and a k value that minimizes an error evaluation value presented below is calculated. Thus, the most reliable direction in which a gradient in brightness changes from a light to a shade can be determined.

$$E(k) = \sum_{i=1}^{M} |\phi_{ik}| \quad (8)$$

At step S5, a direction determined as the direction of a lumen is regarded as an inserting direction. Arrow information shown in FIG. 4 is then superposed on an image, and the resultant image is displayed on the display device 21. Control is then returned to step S1, and the same steps are repeated for image data representing the next frame.

According to the present embodiment, N determining the size of a neighborhood shown in FIG. 10 is set to 5. Alternatively, N may be set to a larger value (for example, 17). A gradient in brightness in a larger area may be detected. Prior to calculation of a gradient vector using sampling-pixels, low-pass filtering (so-called blue masking) may be performed as pre-processing. In this case, an adverse effect of noise or a mucosal structure such as vessels can be eliminated and precision in detecting an inserting direction can be improved.

Moreover, a sum total of values of the angle φik expressed as expression (8) is adopted for error evaluation. Needless to say, the expression (8) may be replaced with another function of the angle φik.

Moreover, a threshold may be used to evaluate the sampling-pixel P shown in FIG. 10 and the neighbor pixels A to H required to calculate a gradient vector in order to eliminate an adverse effect of a halation or prevent incorrect detection. More particularly, the value of each of pixels that are contained in a local domain having a size of N rows and N columns and that include the pixels A to H and P is compared with a threshold THL (for example, THL equals 250). If any pixel value exceeds the THL value, the location of the sampling-pixel P is changed or the sampling-pixel P is unused to detect an inserting direction.

If the magnitude |Vi| equals 0, it means that a gradient in brightness is a nil. The gradient vector Vi is therefore unused to detect an inserting direction. Specifically, the angle φik at which an inverse vector of a gradient vector Vi meets a vector Qk is not calculated according to expression (7) but is set to 0 irrespective of what value k assumes, that is, φi1=φi2=...=φiK=0. (The value of a sampling-pixel whose gradient vector has a magnitude |Vi| of 0 does not contribute to the result of expression (8)).

During direction-of-lumen detection to be performed at step S4, the direction (angle) Vθ of a gradient vector V representing a change in brightness is employed. Since there is a high probability that a lumen may be found in a direction in an endoscopic image in which brightness changes greatly, the magnitude |V| may be utilized. Specifically, gradient vectors Vi (1≦i≦M) are calculated for M sampling-pixels, and a maximum magnitude max|Vi| out of the magnitudes of the gradient vectors is detected. All the vectors Vi are then normalized as expressed as follows:

$$\alpha i = |Vi|/\max |Vi| \quad (9)$$

In expression (9), the αi value of the i-th gradient vector Vi that has the maximum magnitude max|Vi| equals 1. The αi value of any other gradient vector (whose magnitude, |Vi| is not equal to 0) is larger than 0 and smaller than and equal to 1. When the αi value is utilized as a weight coefficient, the expression (8) is rewritten as follows:

$$E(k) = \sum_{i=1}^{M} \left( \frac{|\phi_{ik}|}{\alpha_i} \right) \quad (10)$$

Sampling-pixels are, as shown in FIG. 9, equally selected from all over data of an entire image. Alternatively, as shown in FIG. 13, a center of an image may be excluded, and sampling-pixels may be selected from data of a marginal part of the image which contains a larger amount of brightness change information representing a change in brightness oriented in the direction of a lumen.

As shown in FIG. 14, image data may be divided into domains, and an inserting direction may be detected through processing that is performed on a direction associated with each domain as mentioned below. Referring to FIG. 14, sampling-pixels are selected from the division domains in the marginal part of the image data. The division domains are associated with the directions shown in FIG. 11 and FIG. 15 on a one-to-one basis (the center part of the image data is excluded).

Referring to FIG. 15, points U1 to U8 are points on the outline of an image that are obtained by trisecting the horizontal and vertical lengths of the outline. A division of the outline defined with a pair of points U1 and U3, U1 and U2, U2 and U4, U3 and U5, U4 and U6, U5 and U7, U7 and U8, or U6 and U8 is associated with the same direction as point Q1, Q2, ... Q7, or Q8 shown in FIG. 11, respectively.

A domain in which a change in brightness occurring in a direction associated with the domain is the largest is detected, and the associated direction is determined as an inserting direction. Specifically, Mk sampling-pixels contained in each domain k (1≦k≦K) are projected to points Qk on a division of the outline associated with the domain. A sum total of the magnitudes of vectors directed from the sampling-points to the points Qk associated with each domain k of the vectors (an example is shown in FIG. 16) is calculated as follows:

$$\xi(k) = \sum_{j=1}^{M_k} \left( |\underline{V_j}| \times \cos\phi_{jk} \right) \quad (11)$$

The sum total ξ(k) is calculated relative to all domains, and a direction associated with a domain that gives the largest sum total ξ(k) is regarded as an inserting direction.

As described above, the inserting direction detecting method of the first embodiment of the present invention, and the inserting direction detecting system that presents inserting direction information to an operator on the basis of the result of processing performed according to the method can provide an operator, who is unskilled in endoscopic examination, with insertion aid information. Consequently, the endoscopic examination can be performed smoothly.

Second Embodiment

Figure 17:
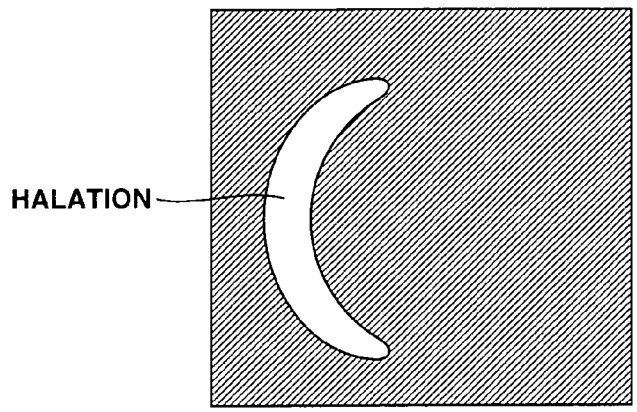
FIG. 17 is an explanatory diagram concerning an arc-shaped halation employed in a second embodiment of the present invention.
Figure 18:
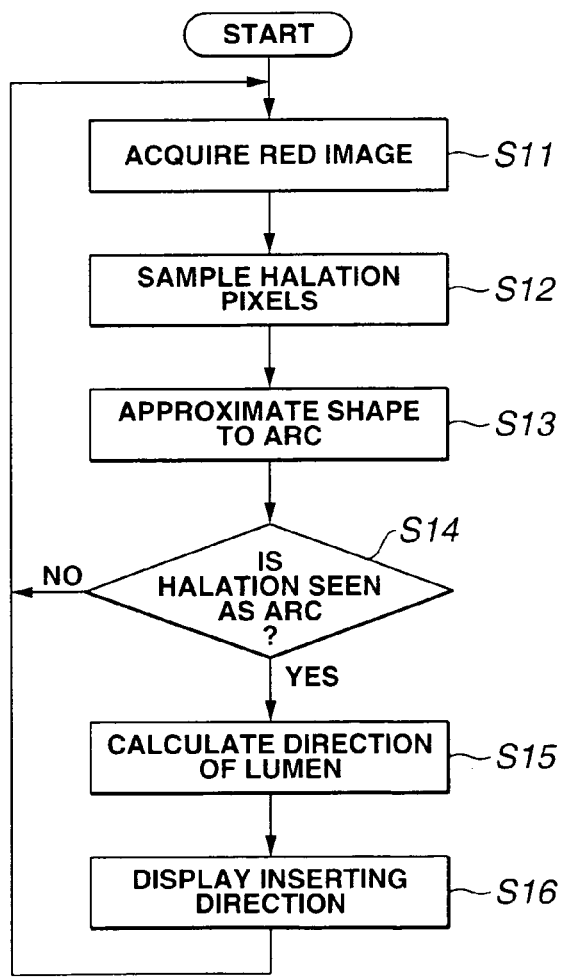
FIG. 18 is a flowchart describing inserting direction detection that is performed in consideration of the halation described in FIG. 17.
Figure 19:
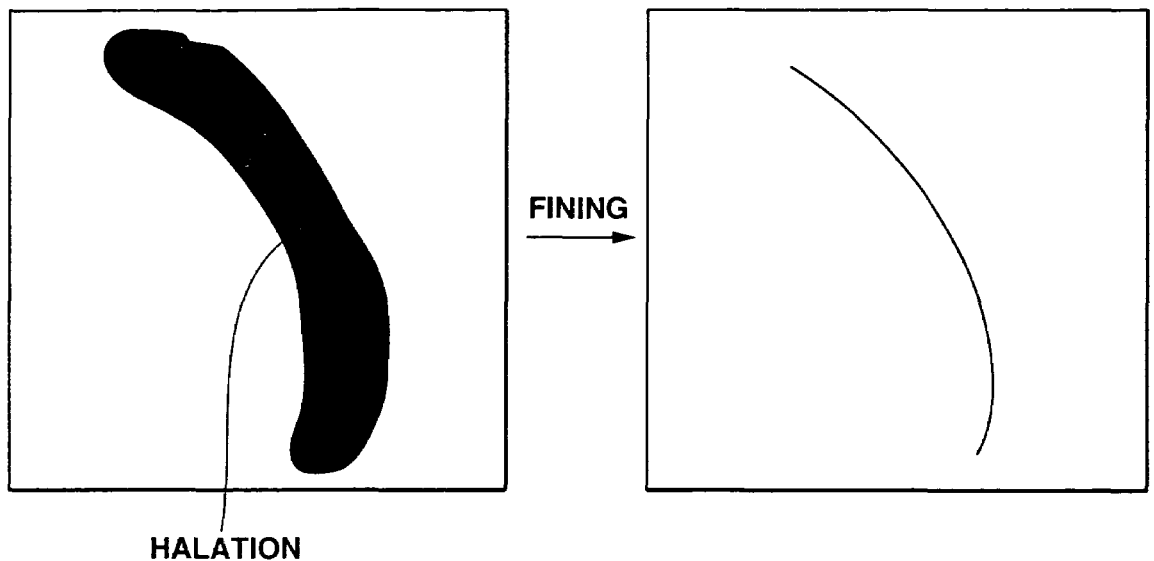
FIG. 19 is an explanatory diagram concerning fining that is performed during the processing described in FIG. 18.
Figure 20:
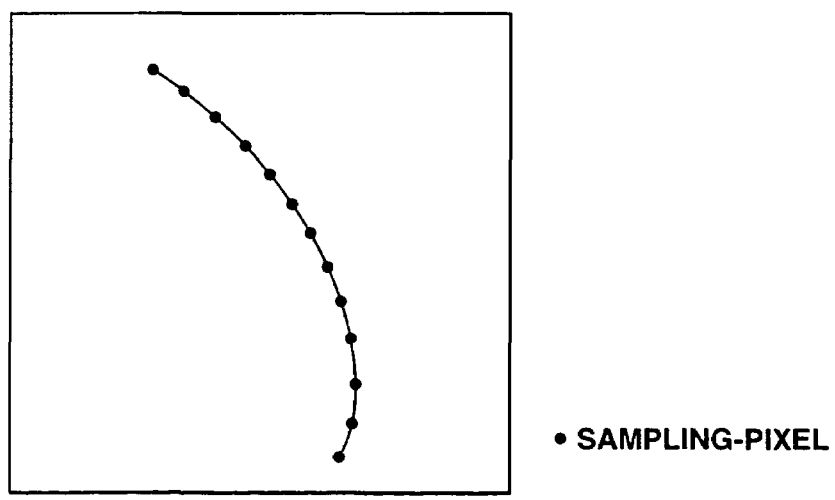
FIG. 20 is an explanatory diagram concerning sampling that is performed during the processing described in FIG. 18.
Figure 21:
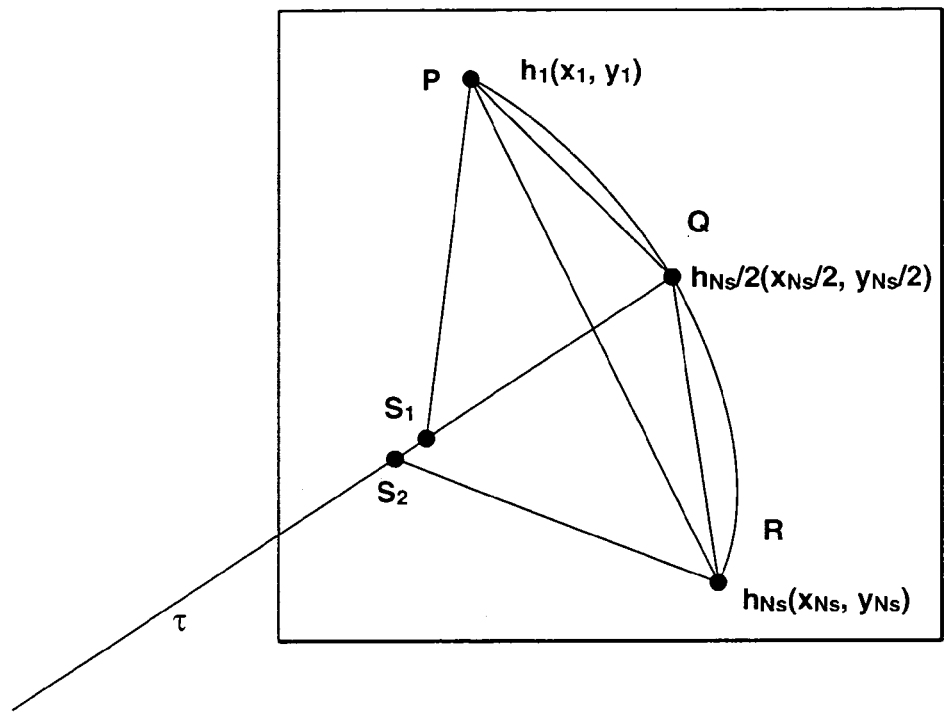
FIG. 21 is an explanatory diagram concerning approximation of the shape of a halation to an arc that is performed during the processing described in FIG. 18.
Figure 22:
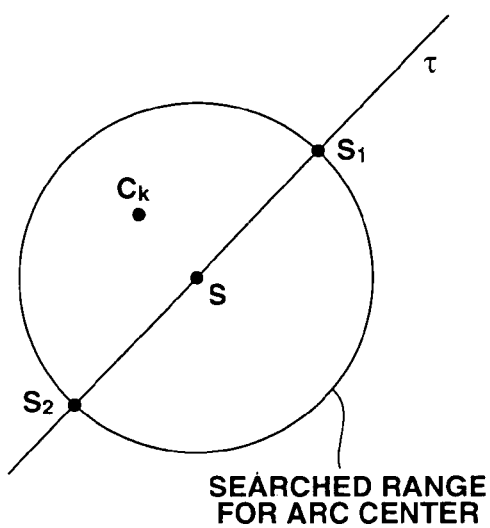
FIG. 22 is an explanatory diagram concerning a range of searched pixels that is defined to extend around an arc center for the purpose of approximation to be performed during the processing described in FIG. 18.

FIG. 17 to FIG. 25 are concerned with a second embodiment of the present invention. FIG. 17 is an explanatory diagram concerning a halation seen as an arc. FIG. 18 is a flowchart describing inserting direction detection to be performed in consideration of the halation shown in FIG. 17. FIG. 19 is an explanatory diagram concerning fining to be performed during the processing described in FIG. 18. FIG. 20 is an explanatory diagram concerning sampling to be performed during the processing described in FIG. 18. FIG. 21 is an explanatory diagram concerning approximation of the shape of the halation to an arc which is performed during the processing described in FIG. 18. FIG. 22 is an explanatory diagram concerning a searched range around an arc center for the purpose of approximation to be performed during the processing described in FIG. 18. FIG. 23 is an explanatory diagram concerning a method of determining the direction of a lumen during the processing described in FIG. 18. FIG. 24 is an explanatory diagram concerning expansion to be performed during the processing described in FIG. 18. FIG. 25 is an explanatory diagram concerning the contents of the processing described in FIG. 18 which are adopted when a plurality of halations is seen.

The second embodiment is nearly identical to the first embodiment. Differences alone will be described below. The same reference numerals will be assigned to components identical to those of the first embodiment, and the description of the components will be omitted.

Described as the second embodiment of the present invention is an inserting direction detecting method that when a lumen disappears from a field of view for imaging, determines the direction of the lumen on the basis of the property of the shape of a halation stemming from reflection from a mucosal surface or the like. Also described is an inserting direction detecting system that presents inserting direction information to an operator according to the result of the processing performed according to the method and thus assists in performing endoscopic examination smoothly.

In endoscopic examination, a phenomenon that is generally known as a halation occurs. Specifically, because of intense mirror reflection caused by a mucosal surface or the like opposed to the distal end of an endoscope, an output signal of a CCD is saturated or a signal component representing the mucosal surface assumes an apparently higher level than the other components representing the surroundings. An endoscopic view image of the large intestine or any other organ having a lumen may suffer from an arc halation.

For example, in the inserted state shown in FIG. 7, an arc halation shown in FIG. 17 occurs. Since there is a high possibility that the direction of the center of the arc agrees with the direction of a lumen, a skilled doctor utilizes the arc halation as insertion aid information and keeps inserting an endoscope rightward within a field of view for imaging.

In the present embodiment, an image processing technique is adopted in order to judge whether a halation occurring in an image is seen as an arc. If so, the direction of the center of the arc is inferred and utilized as inserting direction information.

The configurations of an endoscope system and an inserting direction detecting system in accordance with the present embodiment are identical to the endoscope system and the inserting direction detecting system of the first embodiment. The contents of the main program 26 are different. The contents of image processing to be executed by running the main program 26 will be detailed below.

FIG. 18 is a flowchart describing inserting direction detection described in the main program 26 employed in the present embodiment. At step S11, similarly to step 1 described in FIG. 8 in relation to the first embodiment, a red image out of red, green, and blue images constituting an endoscopic image is acquired. Alternatively, the green or blue image or a luminance image may be used to perform processing identical to the one described below.

At step S12, pixels constituting the received data of the red image are binary-coded using a threshold, and halation pixels are sampled. Specifically, a binary-coded image H is produced based on the value r(x, y) of each pixel whose location is represented by coordinates (x, y) ($0 \leq x < ISX$, $0 \leq y < ISY$). The value of each pixel h(x, y) contained in the image H is set to 1 or reset to 0 as follows:

$h(x, y)=1$ if $r(x, y) \geq THL$ $h(x, y)=0$ if $r(x, y) < THL$ (12)

where the threshold THL may be set to 255 or set to 240 in order to provide a little tolerance. The setting of the threshold THL is modified appropriately. This is because even if a pixel value does not equal to a maximum value of 255, a halation may be discerned.

At step S13, the binary-coded image H is used to judge if the halation is seen as an arc. This is because since a halation is not always seen as an arc, it must be judged whether the halation can be used to detect an inserting direction.

According to the present embodiment, a circle to which a sampled halation is approximated is determined by varying a parameter that is the position of a center or a radius so as to search for an optimal position and an optimal radius. An error of the shape of the halation that is an object of processing from an arc defined with an equation is evaluated.

First, known fining is performed as pre-processing to be performed on the halation image H (if the halation has branches or the like, regeneration is also performed). FIG. 19 shows an example of the result of fining performed on the halation image (in FIG. 19, black is associated with a pixel value of 1).

Incidentally, regeneration is described in, for example, "Guide to Computer Image Processing" (P.75-83, supervised by Hideyuki Tamura, compiled by Industrial Technology Center of Japan, published by Soken Publishing, sold by Seiun Co. Ltd.).

Fined pixels whose locations are represented by coordinates h(x, y) and which suffer from the halation are sampled. For sampling, pixels suffering from both ends of the halation and a middle point between the ends are determined, and NS pixels whose locations are represented by coordinates h(x, y) are sampled nearly equidistantly to one another. The Ns sampling-pixels whose locations are represented by coordinates h(x, Y) shall be regarded as pixels hj(xj, yj) where $1 \leq j \leq Ns$. FIG. 20 shows an example of sampling. The sampling is intended to shorten the time required for calculation, and can be omitted as long as the performance of the CPU 23 is satisfactory.

Next, the pixels hj(xj, yj) that are fined and sampled are checked to judge whether a halation is seen as an arc through the processing composed of steps described below.

First, a searched range within which the center of a circle to which the shape of a halation is approximated and the radius thereof are searched for is defined. As shown in FIG. 21, a triangle PQR is defined with pixels h1(x1, y1), hNs/2(x Ns/2, y Ns/2), and hNs(x Ns, y NS), and a half line τ orthogonal to a side PR is defined to have a point Q as a limit thereof. As shown in FIG. 22, points S1 and S2 satisfying PS1=QS1 and PS2=QS2 are defined on the half line τ. A circle whose center coincides with a middle point S (represented by coordinates (xs, ys)) between the points S1 and S2 and whose radius r equals s/2 (where s is a length of S1S2) is defined as a searched range of the center. K center-point candidates Ck ($1 \leq K$, $1 \leq k \leq K$) are determined. The radius rk of a center having a center-point candidate Ck as its center is determined based on the candidate Ck and set to CkQ, that is, rk=CkQ. Assuming that the position of a center-point candidate Ck is represented by coordinates (cxk, cyk), an error evaluation value for each of Ns pixels hj(xj, yj) relative to the circle Ck is calculated as follows:

$$\varepsilon(k) = \frac{1}{N_s}\left[\sum_{j=1}^{N}\{(x_j - c_{xk})^2 + (y_j - c_{yk})^2 - r_k^2\}\right] \quad (13)$$

K error evaluation values ε(k) are calculated according to the expression (13). The minimum error evaluation value min(ε(k)) is compared with a threshold THE adopted as a criterion for judging whether the shape of a halation is recognized as an arc. If the minimum error evaluation value min($\epsilon$(k)) is smaller than the threshold THE, the shape of the halation is judged to be arc.

$$\min(\epsilon(k)) < THE \quad (14)$$

At step S14, if the condition (14) is satisfied, control is passed to step S15. If not, control is returned to step S11. It is then judged whether control is passed in order to execute processing for image data representing the next frame.

At step S15, the direction of a lumen is determined. The direction of a lumen substantially agrees with the direction of the center of an arc to which the shape of a halation is approximated. Therefore, a half line $\tau$k is defined to link the center Ck of a circle Ck relative to which the error evaluation value is minimum and the point Q shown in FIG. 21 is defined as shown in FIG. 23 (an equation of a straight line is easily defined using coordinates representing two points and the description of the equation is therefore omitted). A point of intersection T at which the half line $\tau$k intersects the outline of an image is defined. As for four sides constituting the outline of an image, the horizontal and vertical lengths are, as shown in FIG. 15, trisected (ISX/3, ISY/3). The resultant divisions of the outline are associated with the eight directions shown in FIG. 4. It is then judged on which of the divisions the point of intersection T lies. An inserting direction is determined based on the division on which the point of intersection T lies. Referring to FIG. 23, the point of intersection T lies on a division associated with the left downward direction (the direction associated with the point Q6 in FIG. 11).

At step S16, similarly to step S5 performed in the first embodiment, arrow information indicating the determined inserting direction is superposed on an image, and the resultant image is displayed on the display device 21. Control is then returned to step S11, and the same steps are performed on image data representing the next frame.

As mentioned above, according to the inserting direction detecting method of the second embodiment of the present invention, and the inserting direction detecting system that presents inserting direction information to an operator on the basis of the result of processing performed according to the method, insertion aid information can be provided for an operator who is unskilled in endoscopic examination. Consequently, endoscopic examination can be performed smoothly.

Moreover, since it is judged whether the shape of a halation is suitable for detection of the direction of a lumen, incorrect inserting direction aid information will not be displayed.

The binary-coded image H of a halation may, as shown in FIG. 24A, have a complex outline. This may cause lots of unnecessary jumps of control after fining is completed. In this case, known expansion is performed. Consequently, the outline is smoothed as shown in FIG. 24B. Thereafter, fining is performed (for expansion and fining, refer to, for example, "Guide to Computer Image Processing" (P.75–83, supervised by Hideyuki Tamura, compiled by Industrial Technology Center of Japan, published by Souken Publishing Co. Ltd., sold by Seiun Co. Ltd.).

In the present embodiment, the center Ck of an arc is searched and determined. Alternatively, a Hough conversion technique or any other shape sampling technique may be adopted.

Moreover, if an image suffers from a plurality of halations as shown in FIG. 25A, a series of the processing to which the present embodiment is adapted is performed with the fined pixels serving as limits hk and hk+1 of the halations linked as shown in FIG. 25B. Whether the limit hk +1 lies within a circle whose center coincides with the limit hk and whose radius is expressed as rhk (rhk is set to an appropriate value, for example, 20) is checked based on coordinates representing the limit hk in order to judge whether linkage is feasible.

Third Embodiment

Figure 27:
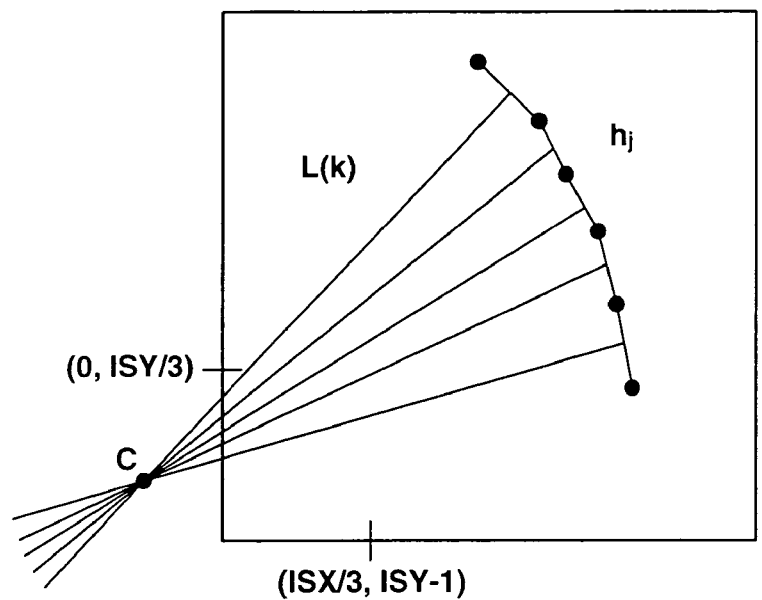
FIG. 27 is an explanatory diagram concerning a method of determining the direction of a lumen during the processing described in FIG. 26.
Figure 28:
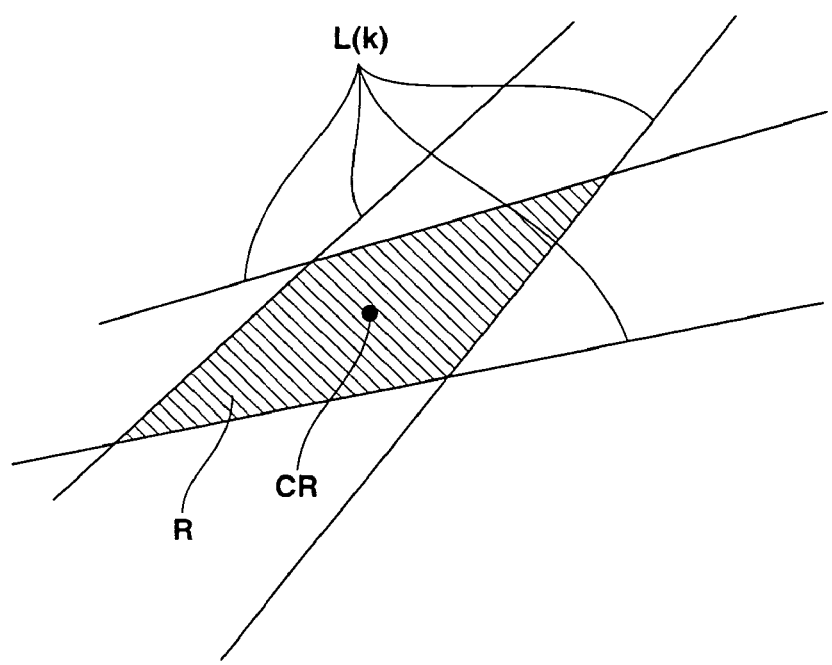
FIG. 28 is an explanatory diagram concerning judgment of an arc shape that is performed during the processing described in FIG. 26.

FIG. 26 to FIG. 28 are concerned with a third embodiment of the present invention. FIG. 26 is a flowchart describing inserting direction detection. FIG. 27 is an explanatory diagram concerning a method of determining the direction of a lumen during the processing described in FIG. 26. FIG. 28 is an explanatory diagram concerning arc shape judgment to be performed during the processing described in FIG. 26.

The third embodiment is nearly identical to the first embodiment. Differences alone will be described. The same reference numerals will be assigned to components identical to those of the first embodiment, and the description of the components will be omitted.

As the third embodiment of the present invention, a description will be made of another method of detecting an inserting direction by utilizing the property of the shape of a halation, which has been described in relation to the second embodiment, in case a lumen disappears from a field of view for imaging. Also described is an inserting direction detecting system that assists in realizing smoother endoscopic examination by presenting inserting direction information to an operator on the basis of the result of processing performed according to the method.

An endoscope system and an inserting direction detecting system in accordance with the present embodiment have the same configurations as the one described in relation to the first embodiment and the one in accordance with the first embodiment. The contents of the main program 26 are different. Therefore, the contents of image processing to be performed as described in the main program 26 will be described below.

FIG. 26 is a flowchart describing inserting direction detection described in the main program 26. At step S21, similarly to step S1 described in FIG. 8 according to the first embodiment, a red image is acquired from among red, green, and blue images constituting a received endoscopic image. The green or blue image or a luminance image may be used to perform the same processing as the one described below.

At step S22, similarly to step S12 performed according to the second embodiment, halation pixels are sampled in order to produce a binary-coded image H.

At step S23, similarly to step S13 performed according to the second embodiment, fining described in conjunction with FIG. 19 and FIG. 20 is performed on the halation image H. Pixels whose locations are represented by coordinates h(x, y) are generated and sampled. At this time, Ns pixels whose locations are represented by coordinates h(x, y) are sampled so that the pixels will include pixels serving at both limits of the halation and will be arranged equidistantly. Hereinafter, the Ns sampling-pixels whose locations are represented by coordinates h(x, y) shall be described as pixels hj(xj, yj) where $1 \leq j \leq Ns$ is satisfied.

According to the present embodiment, a line L(k) perpendicular to the midpoint of a segment linking each of pixel pairs selected from among the sampling-pixels hj(xj, yj), that is, pairs of pixels h1(x1, y1) and h2(x2, y2), pixels h2(x2, y2) and h3(x3, y3) . . . , pixels hNs-2(xNs-2, yNs-2) and hNs-1(xNs-1, yNs-1), and pixels hNs-1(xNs-1, yNs-1) and hNs(xNs, yNs) is defined. Herein, $1 \leq k \leq Ns-1$ is satisfied.

FIG. 27 shows an example of segments L(k) and presents an example of calculation of a candidate for the direction of a lumen. If the pixels hj(xj, yj) lie on an arc, the defined segments L(k) intersects one another at the center C of the arc. A candidate for the direction of a lumen can be determined by associating the position of the center C with any of the eight directions shown in FIG. 4. When the segments L(k) do not intersect one another at one point, a barycenter CR of pixels contained in a closed domain R defined with a plurality of points of intersection as shown in FIG. 28 is calculated and substituted for the center C. The coordinates (Xc, Yc) representing the barycenter CR are expressed as follows:

$$X_c = \frac{1}{N_r} \times \left(\sum_{i=1}^{N_r} x_{ri}\right), \quad Y_c = \frac{1}{N_r} \times \left(\sum_{i=1}^{N_r} y_{ri}\right) \quad (14')$$

where Nr denotes the number of pixels contained in the domain R, and Xri and Yri denote coordinates representing the position of the i-th pixel in the horizontal and vertical directions.

At step S24, it is judged whether the calculated candidate for the direction of a lumen is reliable, that is, whether a halation is seen as an arc. Specifically, the area (number of pixels) Ra of the closed domain R shown in FIG. 28 is compared with a threshold THR. If Ra≦THR is satisfied, the halation is seen as an arc and the calculated candidate for the direction of a lumen is reliable. If Ra>THR is satisfied, the halation is not seen as an arc and the calculated candidate is unreliable.

If it is judged from the result of judgment at step S24 that the candidate for the direction of a lumen is reliable, control is passed from step S25 to step S26. Otherwise, control is returned to step S21. It is judged whether control is passed to a step of processing image data that represents the next frame.

At step S26, similarly to step S5 performed according to the first embodiment, arrow information indicating the calculated inserting direction is superposed on an image. The resultant image is then displayed on the display device 21. Control is then returned to step S21, and the same steps are repeated for the next frame.

As described above, according to the inserting direction detecting method of the third embodiment of the present invention and the inserting direction detecting system that presents inserting direction information to an operator on the basis of the result of processing performed according to the method, insertion aid information can be provided for an operator who is unskilled in endoscopic examination. Consequently, endoscopic examination can be performed smoothly. Moreover, since it is judged whether the shape of a halation is helpful in detecting the direction of a lumen, incorrect inserting direction aid information will never be displayed.

As mentioned above, a candidate for the direction of a lumen is inferred from the coordinates representing the point of intersection of the segments L(k). As shown in FIG. 15, points of intersection at which the segments L(k) intersects a division of the outline of an image may be detected. A direction associated with a division of the outline which the largest number of segments L(k) intersect may be determined as a candidate for the direction of a lumen.

Fourth Embodiment

Figure 29:
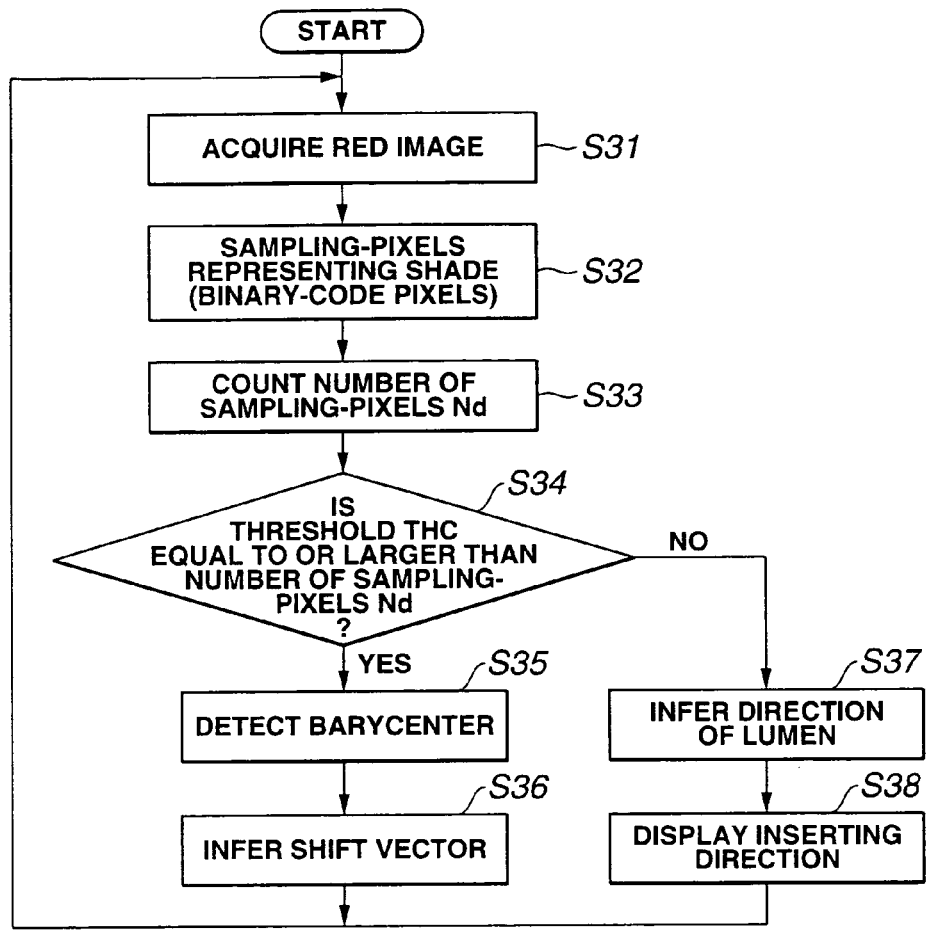
FIG. 29 is a flowchart describing inserting direction detection in accordance with a fourth embodiment of the present invention.
Figure 30A:
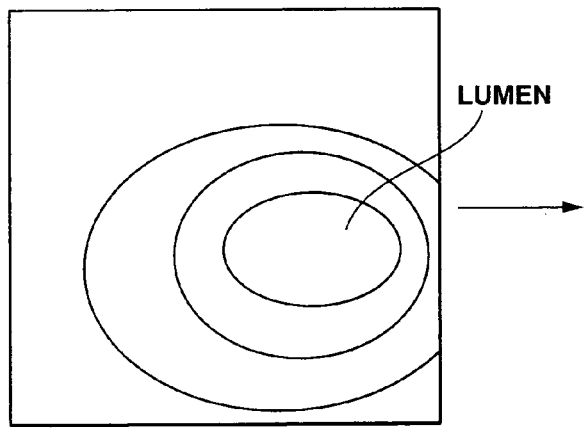
FIG. 30A is an explanatory diagram of a raw image concerning a method of determining the direction of a lumen during the processing in FIG. 29.
Figure 30B:
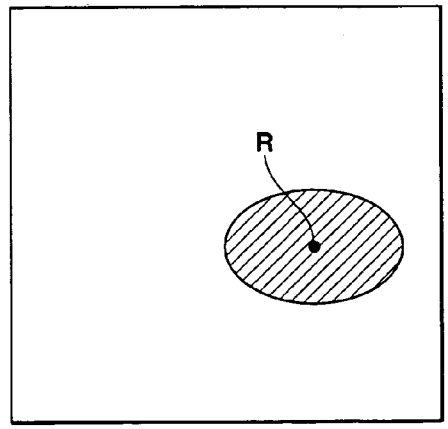
FIG. 30B is a first explanatory diagram concerning a method of determining the direction of a lumen during the processing in FIG. 29.
Figure 31:
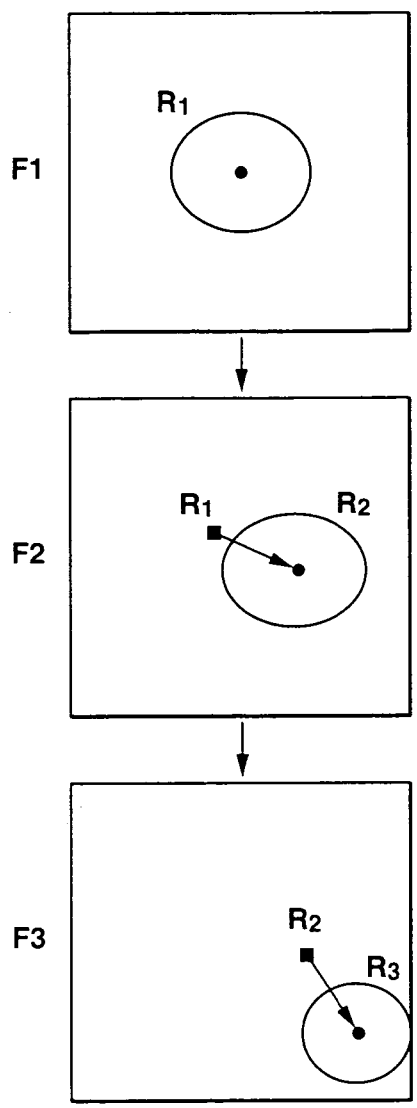
FIG. 31 is a second explanatory diagram concerning a method of determining the direction of a lumen during the processing described in FIG. 29.
Figure 32:
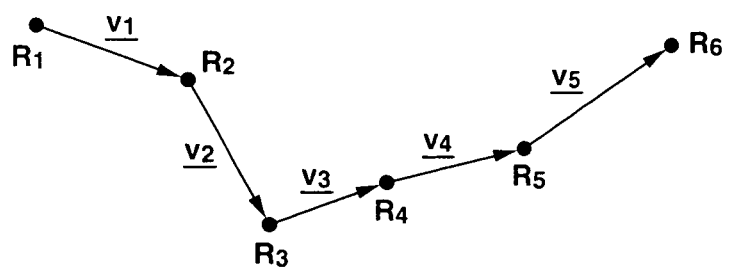
FIG. 32 is a third explanatory diagram concerning a method of determining the direction of a lumen during the processing described in FIG. 29.
Figure 33:
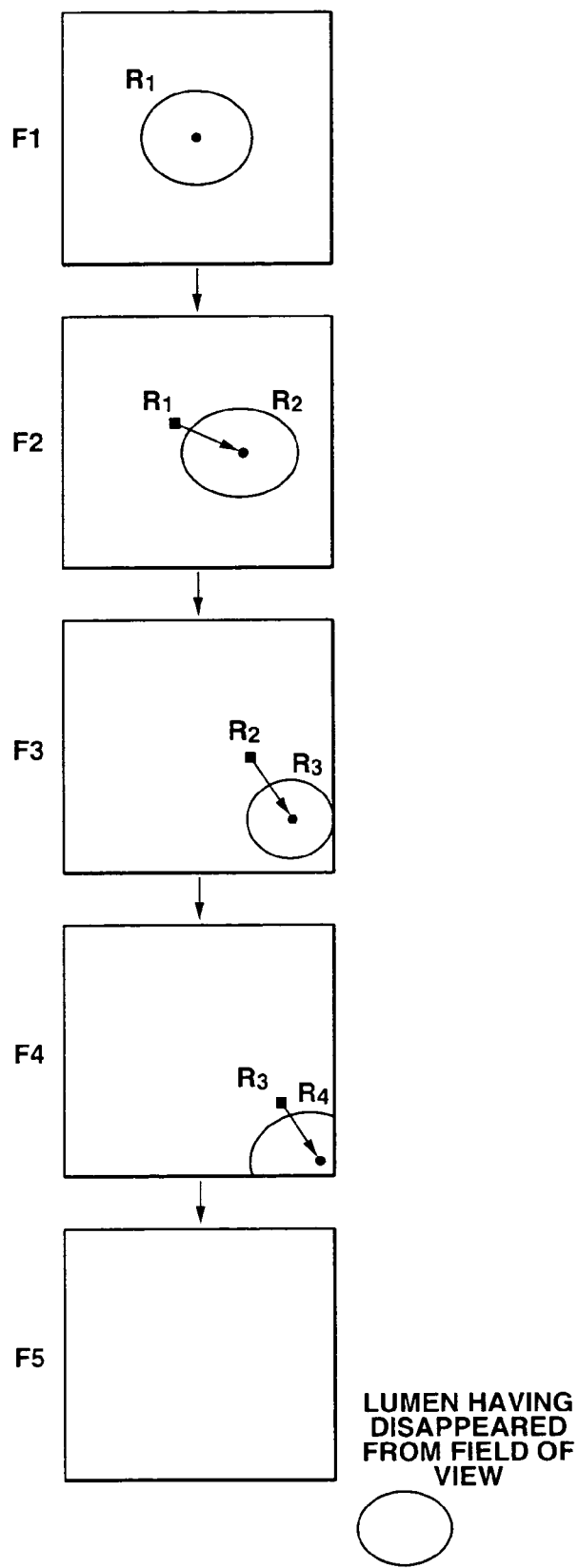
FIG. 33 is a fourth explanatory diagram concerning a method of determining the direction of a lumen during the processing described in FIG. 29.

FIG. 29 to FIG. 33 are concerned with a fourth embodiment of the present invention. FIG. 29 is a flowchart describing inserting direction detection. FIG. 30 is a first explanatory diagram concerning a method of determining the direction of a lumen during the processing described in FIG. 29. FIG. 31 is a second explanatory diagram concerning the method of determining the direction of a lumen during the processing described in FIG. 29. FIG. 32 is a third explanatory diagram concerning the method of determining the direction of a lumen during the processing described in FIG. 29. FIG. 33 is a fourth explanatory diagram concerning the method of determining the direction of a lumen during the processing described in FIG. 29.

The fourth embodiment is nearly identical to the first embodiment. Differences alone will be described. The same reference numerals will be assigned to components identical to those of the first embodiment, and the description of the components will be omitted.

Described as the fourth embodiment of the present invention is an inserting direction detecting method according to which if a lumen disappears from a field of view for imaging, the direction of the lumen is determined based on a time-sequential shift of a view seen within a field of view from a view containing the lumen. Also described is an inserting direction detecting system capable of assisting in performing endoscopic examination smoothly by presenting inserting direction information to an operator on the basis of the result of processing performed according to the method.

FIG. 29 is a flowchart describing inserting direction detection that is executed according to the main program 26 employed in the present embodiment. At step S31, similarly to step S1 described in FIG. 8 in relation to the first embodiment, a red image is acquired from among the red, green, and blue images constituting a received endoscopic image. Alternatively, the green or blue image or a luminance image may be used to perform processing identical to the one described below. At step S32, in order to detect a lumen within a field of view, binary-coded pixels representing a shade are sampled using a threshold THD. Specifically, a binary-coded image D is produced based on values r(x, y) of pixels whose locations are represented by coordinates (x, y) (0≦x<I SX, 0≦y<I SY). The values of the pixels d(x, y) constituting the binary-coded image D meet the following condition:

d(x, y)=1 if r(x, y)≦THD d(x, y)=0 if r(x, y)>THD   (15)

where the threshold THD is set to, for example, 20.

At step S33, the number of pixels having a value of 1 and being contained in the binary-coded image D, that is, the number of pixels representing the shade, Nd, is calculated.

At step S34, the number of pixels Nd calculated at step S33 is compared with the threshold THL in order to determine whether the number of pixels representing the shade is large enough to judge that a lumen is found in a field of view. The threshold THL is, according to the present embodiment, set to 10% of the number of all pixels. Namely,

THL=(ISX×ISY)/10   (16)

If Nd≧THL is satisfied, control is passed to step S35. Otherwise, control is passed to step S37.

At step S35, a barycenter R among the Nd sampling-pixels representing the shade that may a lumen found in a field of view is calculated. FIG. 30 shows an example of the barycenter R. Pixels representing a shade are sampled from data of a raw image (red image) shown in FIG. 30A using a threshold. A domain that is a hatched part of FIG. 30B and that may represent a lumen is defined, and the barycenter R of the domain is calculated.

At step S36, a shift vector representing a shift of the barycenter R is inferred from a change in the position of the barycenter R from the position thereof calculated from image data of the previous frame. A description will be made in conjunction with FIG. 31. Referring to FIG. 31, F1, F2, and F3 denote frames to be received time-sequentially. A barycenter of a domain representing a shade of a lumen visualized in the frame F1 shall be R1 and coordinates representing the position of the barycenter R1 shall be (xr1, yr1). Likewise, a barycenter of a domain representing the shade visualized in the frame F2 shall be R2 and coordinates representing the position of the barycenter R2 shall be (xr2, yr2). A shift vector v1 tracing a shift of the lumen within a field of view is calculated as follows:

$$v1=(xr2-xr1, yr2-yr1) \quad (17)$$

Likewise, a shift vector v2 relevant to a change from the frame F2 to the frame F3 is calculated. Barycenters Ri and shift vectors v1 (where i denotes an integer equal to or larger than 1) are stored. Thus, a change in the position of a barycenter of data representing a lumen can be traced as shown in FIG. 32.

If a lumen is unseen within a field of view for imaging, control is passed from step S34 to step S37. The direction of a lumen is inferred.

Assuming that a lumen is visualized in a frame Fi but has disappeared from a field of view for producing a frame Fi+1, there is a high possibility that the lumen may be found in the direction of an immediately preceding shift vector vi. Therefore, a direction closest to the direction of the shift vector vi is adopted as an inserting direction. Consequently, the lumen is caught in the field of view. For example, when a frame F5 shown in FIG. 33 is produced from a field of view, the right downward direction associated with the point Q8 shown in FIG. 11 is adopted as an inserting direction. In order to determine a direction closest to the direction of a barycenter Ri, an angle is evaluated using an expression similar to the expression (7) described in relation to the first embodiment.

At step S38, similarly to step S5 performed according to the first embodiment, arrow information indicating an inserting direction is superposed on an image, and the resultant image is displayed on the display device 21. Control is then returned to step S21, and the same steps are repeated for image data representing the next frame.

As mentioned above, according to the inserting direction detecting method of the fourth embodiment of the present invention and the inserting direction detecting system that presents inserting direction information to an operator on the basis of processing performed according to the method, if a lumen disappears from a field of view for imaging, the direction of the lumen is detected based on a time-sequential shift of a view seen within the field of view. Inserting direction information can be presented to an operator. Consequently, insertion aid information can be provided for an operator who is unskilled in endoscopic examination. Thus, endoscopic examination can be achieved smoothly.

The number of sampling-pixels Nd is counted at step S33. At this time, labeling as well as contraction and expansion may be performed as pre-processing in order to remove pixels sampled as, for example, those representing a shade on the margin of an image caused by irregular illumination other than a shade of a lumen. Thus, a minor domain of sampling-pixels may be removed.

Incidentally, the labeling is disclosed in, for example, "Guide to Computer Image Processing" (P.75–83, supervised by Hideyuki Tamura, compiled by Japan Industrial Technology Center, published from Souken Publishing Co., Ltd., sold by Seiun Co., Ltd.).

Fifth Embodiment

Figure 34:
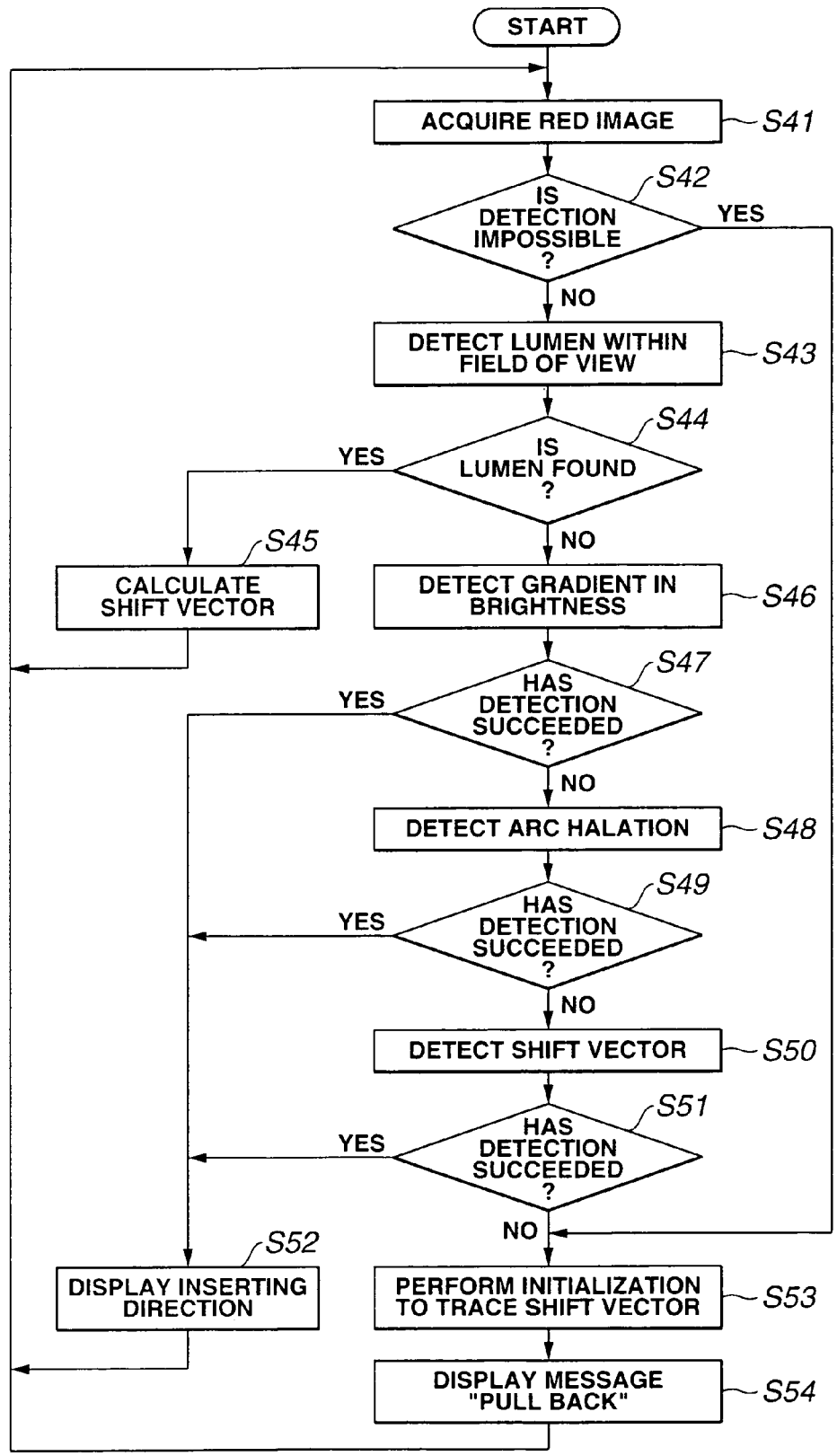
FIG. 34 is a flowchart describing inserting direction detection in accordance with a fifth embodiment of the present invention.
Figure 35:
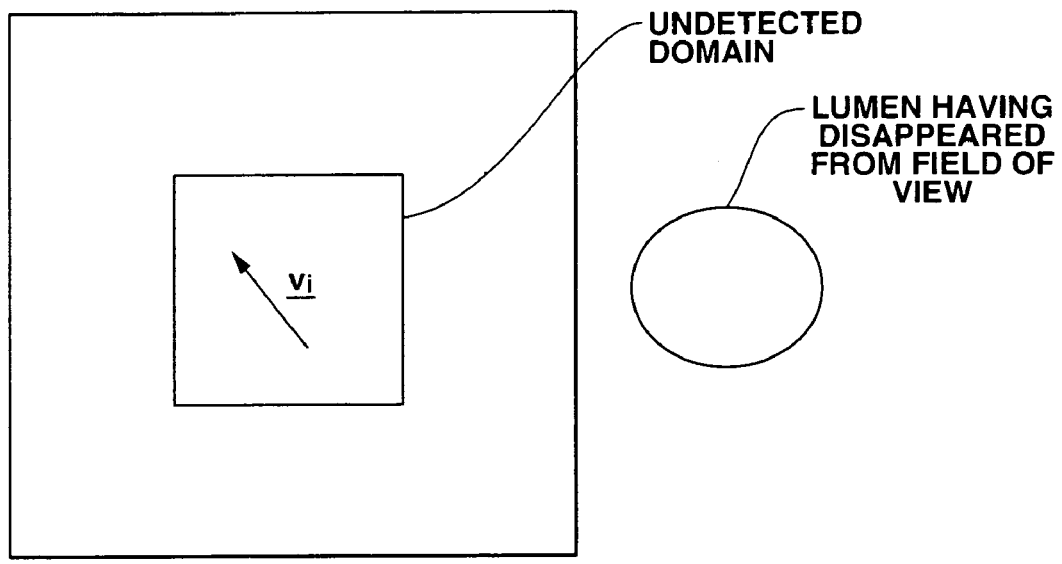
FIG. 35 is an explanatory diagram concerning a case where direction-of-lumen detection based on a shift vector is judged to be inappropriate during the processing described in FIG. 34.
Figure 36:
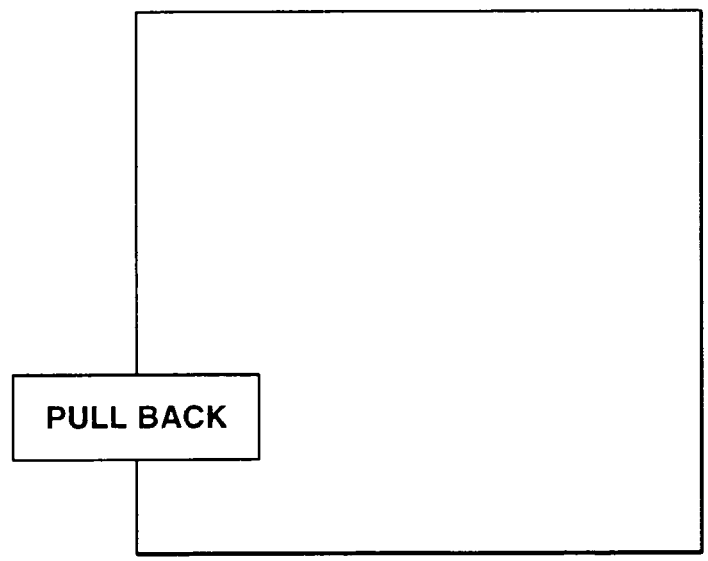
FIG. 36 is an explanatory diagram concerning display of a result when inserting direction detection described in FIG. 34 is inappropriate or unfeasible.

FIG. 34 to FIG. 36 are concerned with a fifth embodiment of the present invention. FIG. 34 is a flowchart describing inserting direction detection. FIG. 35 is an explanatory diagram concerning a case where direction-of-lumen detection based on a shift vector is judged to be undesirable during the processing described in FIG. 34. FIG. 36 is an explanatory diagram concerning display of a result which is performed when it is undesirable or unfeasible to perform inserting direction detection during the processing described in FIG. 34.

The fifth embodiment is nearly identical to the first embodiment. Differences alone will be described. The same reference numerals will be assigned to components identical to those of the first embodiment, and the description of the components will be omitted. Described as the fifth embodiment of the present invention are an inserting direction detecting method and an inserting direction detecting system capable of improving precision by selecting an inserting direction detecting method optimal to an endoscopic image to be processed.

In the first to fourth embodiments of the present invention, a description has been made of various direction-of-lumen detecting methods based on a gradient in brightness within a field of view for imaging, the property of the shape of a halation, or a shift of a view seen within a field of view. On the other hand, a scene visualized in an endoscopic image varies diversely. In order to effectively utilize the detecting methods, an optimal detecting method must be selected according to a scene.

Referring to the drawings, the inserting direction detecting method and inserting direction detecting system in accordance with the present embodiment will be described below.

FIG. 34 is a flowchart describing actions to be performed by the inserting direction detecting system 12 in accordance with the present embodiment.

At step S41, similarly to step S1 described in FIG. 8 in relation to the first embodiment, a red image is acquired from among red, green, and blue images constituting a received endoscopic image. The green or blue image or a luminance image may be used to perform the same processing as the one described below.

At step S42, it is judged whether a lumen visualized in the received endoscopic image can be found within a field of view or the direction of a lumen can be detected in the received endoscopic image. As far as the large intestine is examined using the endoscope, if the endoscope is approached too closely to the mucosa, the endoscope becomes out of focus. Besides, there is a scene that is visualized in red alone (called a "red ball" among endoscopists).

It is undesirable to display an inserting direction in the image of the scene (the inserting direction can be detected according to the method of the fourth embodiment that traces a shift vector, but priority must be given to reliable insertion). The endoscope 1 must be withdrawn (pulled back) once so that a lumen can be caught in a field of view.

The red-ball state is very rare and can be identified by checking within what range an average of pixel values constituting the data of the entirely red image falls or a standard deviation of each of the pixel values falls. Otherwise, green image data may also be employed, and an average of pixel values constituting each of red and green image data and a standard deviation of each of the pixel values may be checked.

If it is judged at step S42 that a lumen within a field of view or the direction of the lumen cannot be detected, control is passed to step S53. Otherwise, control is passed to step S43.

At step S43, it is detected whether a lumen is seen within the field of view. Herein, the lumen is detected through a series of steps that are performed for sampling pixels representing a shade and that are described steps S32 and S33 in FIG. 29 in relation to the fourth embodiment.

At step S44, similarly to step S34 described in FIG. 29, the result of detection is judged. If it is judged that a lumen is seen within the field of view, control is passed to step S45. At steps similar to steps S35 and S36 included in the fourth embodiment, a shift vector is calculated. Control is then returned to step S41.

On the other hand, if it is judged that a lumen is not seen within the field of view, control is passed to step S46. At step S46, the direction of a lumen is detected based on a gradient in brightness described as a series of steps S2, S3, and S4 in FIG. 8 in relation to the first embodiment. Control is then passed to step S47.

At step S47, it is judged whether detection of the direction of a lumen based on a gradient in brightness which is performed at step S46 has succeeded. Herein, a ratio of the smallest error evaluation value min($\epsilon(k)$), which is calculated according to the expression (8), to the second smallest error evaluation value smin($\epsilon(k)$) (second candidate for the direction of a lumen), that is, min($\epsilon(k)$)/smin($\epsilon(k)$), is compared with a threshold THL. The smaller the ratio min($\epsilon(k)$)/smin($\epsilon(k)$), the higher the reliability of the result of detection. The threshold THL satisfies $0 \leq THL \leq 1$. Herein, the threshold THL shall equal 0.5. If min(($\epsilon(k)$)/smin($\epsilon(k)$) $\leq$ THL is satisfied, the detection is judged to have succeeded. Control is then passed to step S52. Otherwise, control is passed to step S48.

At step S48, direction-of-lumen detection is performed based on the property of the shape of a halation as described in relation to the second or third embodiment. Specifically, a series of steps described as steps S12 to S15 in FIG. 18 or steps S22 to S25 in FIG. 26 is performed, and control is passed to step S49.

At step S49, control is passed depending on whether detection based on the property of the shape of a halation has succeeded. The judgment is identical to the one of step S14 or S25 made depending on whether a halation is seen as an arc. If it is judged that detection has succeeded, control is passed to step S52. Otherwise, control is passed to step S50.

At step S50, direction-of-lumen detection based on a shift vector is performed as described in relation to the fourth embodiment. Specifically, processing similar to step S37 in FIG. 29 is performed in order to detect the direction of a shift of a lumen within a field of view using data of previous frames. Control is then passed to step S51.

At step S51, it is judged whether detection of the direction of a lumen of step S50 has succeeded. A shift vector may be incorrectly detected because of, for example, a change in the shape of an image of the large intestine caused by a change in a patient's posture or an adverse effect of pulsation, an increase in the size of a shade caused by a change in an amount of light stemming from light control, or a change in a view seen within a field of view occurring at a higher rate than a frame rate (normally 1/30 sec) and stemming from abrupt angling or the like. In this case, for example, as shown in FIG. 35, although a shift vector vi is detected in the center of a field of view, a lumen is found outside the field of view in a direction that is not inferred from the shift vector. Therefore, as shown in FIG. 35, an undetected domain is defined in the vicinity of the center of image data. When the shift vector vi is detected within the domain, it is determined that the detection is not performed.

If it is judged at step S51 that direction-of-lumen detection based on a shift vector has succeeded, control is passed to step S52. Otherwise, control is passed to step S53.

At step S52, similarly to step S5 performed in the first embodiment, arrow information indicating an inserting direction is superposed on an image on the basis of the result of detection. Herein, the detection is detection of the direction of a lumen performed based on a gradient in brightness, the property of the shape of a halation, or a shift vector. The resultant image is then displayed on the display device 21. Control is then returned to step S41, and the processing is repeated.

At step S53, since the direction of a lumen cannot be detected in an image to be processed, initialization (discard of shift vector information acquired so far) is performed in order to suspend tracing of a shift vector. Control is then passed to step S53.

At step S54, a message "Pull back." shown in FIG. 36 or the like is displayed on the display device 21 in order to prompt a doctor to temporarily withdraw the endoscope 1 so as to catch a lumen in a field of view or to perform a inserting procedure safely and reliably. Control is then returned to step S41, and a series of the processing is repeated.

As mentioned above, according to the inserting direction detecting method of the fifth embodiment of the present invention and the inserting direction detecting system in which the method is implemented, an optimal inserting direction detecting method is selected and employed depending on an endoscopic image to be processed. This results in smoother endoscopic examination.

The embodiments of the present invention have been described so far. The present invention is not limited to the embodiments. Needless to say, various modifications can be made within the spirit of the present invention.

INDUSTRIAL APPLICABILITY

As described above, according to the present invention, there is provided an endoscope inserting direction detecting method according to which even if a lumen disappears from a field of view, an inserting direction can be detected.

Moreover, there is provided an endoscope inserting direction detecting system that assists in performing endoscopic examination more smoothly by presenting inserting direction information to an operator according to the result of inserting direction detection.

Moreover, it is possible to provide an endoscope inserting direction detecting method capable of prompting an operator to perform manipulations appropriately in case it is hard to detect an inserting direction, such as in case an endoscope has approached too closely the mucosal surface of the large intestine.

The invention claimed is:

1. An endoscope inserting direction detecting system comprising:
   a first step of receiving an endoscopic image;
   a second step of detecting an endoscope inserting direction, in which an endoscope should be inserted, on the basis of the endoscopic image; and
   a third step of producing information concerning the detected inserting direction, wherein;
   a plurality of detecting alogorithms is included in order to detect the insering direction; and
   any of the detecting alogorithms is selected based on the endoscopic image.

2. An endoscope inserting direction detecting system comprising:
   an endoscopic image inputting means for receiving an endoscopic image;
   an inserting direction detecting means including a plurality of detecting algorithms for the purpose of detecting an endoscope inserting direction, in which an endoscope should be inserted, using the endoscopic image; and
   an insertion aid information producing means for producing insertion aid information on the basis of the detected inserting direction, wherein:
   the endoscope inserting direction detecting system further comprises a detecting algorithm changing means for changing detecting algorithms, any of which the inserting direction detecting means adopts, according to the endoscopic image.

3. An endoscope inserting direction detecting system according to claim 2, further comprising a display means on which the insertion aid information is displayed.

* * * * *

UNITED STATES PATENT AND TRADEMARK OFFICE
CERTIFICATE OF CORRECTION

| | |
|---|---|
| PATENT NO. | : 7,258,664 B2 |
| APPLICATION NO. | : 10/797714 |
| DATED | : August 21, 2007 |
| INVENTOR(S) | : Hirokazu Nishimura et al. |

It is certified that error appears in the above-identified patent and that said Letters Patent is hereby corrected as shown below:

<u>Column 23, Line 2, Claim 1:</u>

"system" should read -- method --

Signed and Sealed this

Twentieth Day of November, 2007

JON W. DUDAS
*Director of the United States Patent and Trademark Office*